United States Patent [19]
West et al.

[11] Patent Number: 5,545,200
[45] Date of Patent: Aug. 13, 1996

[54] STEERABLE ELECTROPHYSIOLOGY CATHETER

[75] Inventors: Scott H. West, Tracy; Frank Nguyen, San Jose, both of Calif.

[73] Assignee: Medtronic Cardiorhythm, San Jose, Calif.

[21] Appl. No.: 343,310

[22] Filed: Nov. 22, 1994

Related U.S. Application Data

[63] Continuation-in-part of Ser. No. 95,447, Jul. 20, 1993, abandoned.

[51] Int. Cl.$^6$ .............................. A61M 1/00; A61B 17/38
[52] U.S. Cl. .............................. 607/122; 607/119; 606/29; 606/46; 128/642
[58] Field of Search ...................................... 607/122, 123, 607/116, 119; 604/95, 264, 265, 280; 606/33, 41, 29, 46, 48, 49, 50; 128/642, 668, 670, 695

[56] References Cited

U.S. PATENT DOCUMENTS

| | | |
|---|---|---|
| 2,498,692 | 2/1950 | Mains . |
| 3,528,406 | 9/1970 | Jeckel et al. . |
| 3,557,780 | 1/1971 | Sato . |
| 3,605,725 | 9/1971 | Bentov . |
| 4,277,168 | 7/1981 | Oku . |
| 4,586,923 | 5/1986 | Gould et al. . |
| 4,677,990 | 7/1987 | Neubauer . |
| 4,718,419 | 1/1988 | Okada . |
| 4,777,955 | 10/1988 | Brayton et al. . |
| 4,860,769 | 8/1989 | Fogarty et al. . |
| 4,874,371 | 10/1989 | Comben et al. . |
| 4,886,067 | 12/1989 | Palermo . |
| 4,920,980 | 5/1990 | Jackowski . |
| 4,930,521 | 6/1990 | Metzger et al. . |
| 4,935,017 | 6/1990 | Sylvanowicz . |
| 4,960,134 | 10/1990 | Webster, Jr. . |
| 5,083,565 | 1/1992 | Parins . |
| 5,168,864 | 12/1992 | Shockey . |
| 5,275,151 | 1/1994 | Shockey et al. . |
| 5,318,525 | 6/1994 | West et al. . |
| 5,327,297 | 7/1994 | Avitall . |
| 5,354,297 | 10/1994 | Avitall . |
| 5,364,352 | 11/1994 | Cimino et al. . |
| 5,376,084 | 12/1994 | Bacich et al. . |

FOREIGN PATENT DOCUMENTS

| | | |
|---|---|---|
| WO93/02733 | 2/1993 | WIPO . |
| WO94/11057 | 5/1994 | WIPO . |

*Primary Examiner*—Randall L. Green
*Assistant Examiner*—Perry E. Van Over
*Attorney, Agent, or Firm*—Townsend and Townsend and Crew

[57] ABSTRACT

An electrophysiology catheter (20) comprises a shaft (22) having a first bending stiffness and a deflectable tip (28) secured to the distal end (24) of the shaft with a second bending stiffness less than the first bending stiffness. At least one electrode (34, 36) is mounted to the tip for delivering current to or monitoring electrical activity of tissue. A manipulator wire (58) is coupled to the distal end of the deflectable tip, whereby the deflectable tip may be deflected by axial force applied to the manipulator wire. A stiffener member (66) is axially slidable relative to the tip so as to adjust the tip curvature without removing the catheter from the body. The catheter may further include a core wire (72) configured to rotate the deflectable tip about a longitudinal axis (2) without rotating the proximal end (26) of the catheter shaft, wherein the distal end of the deflectable tip remains in a substantially constant axial position, preferably in a plane perpendicular to the longitudinal axis.

32 Claims, 17 Drawing Sheets

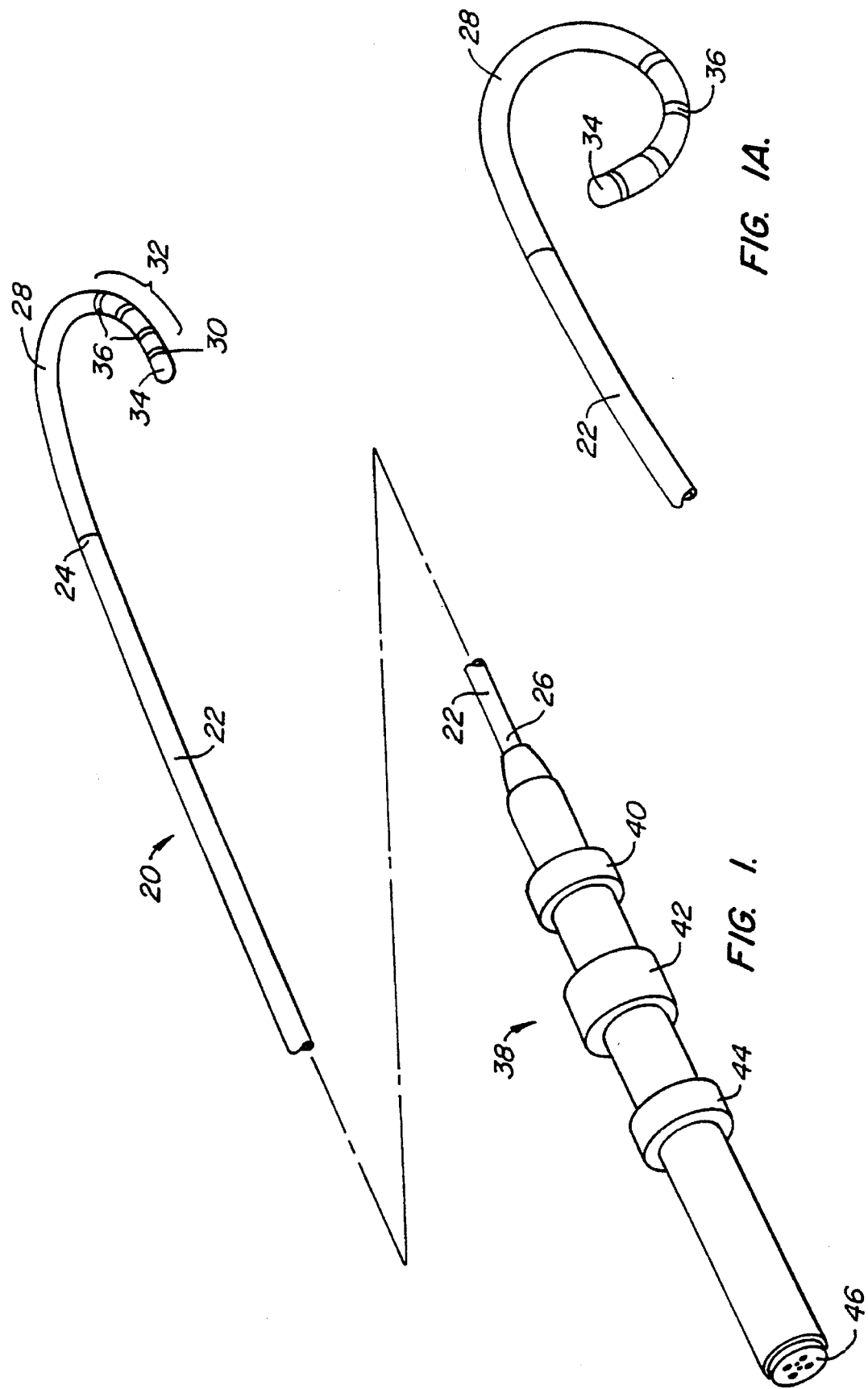

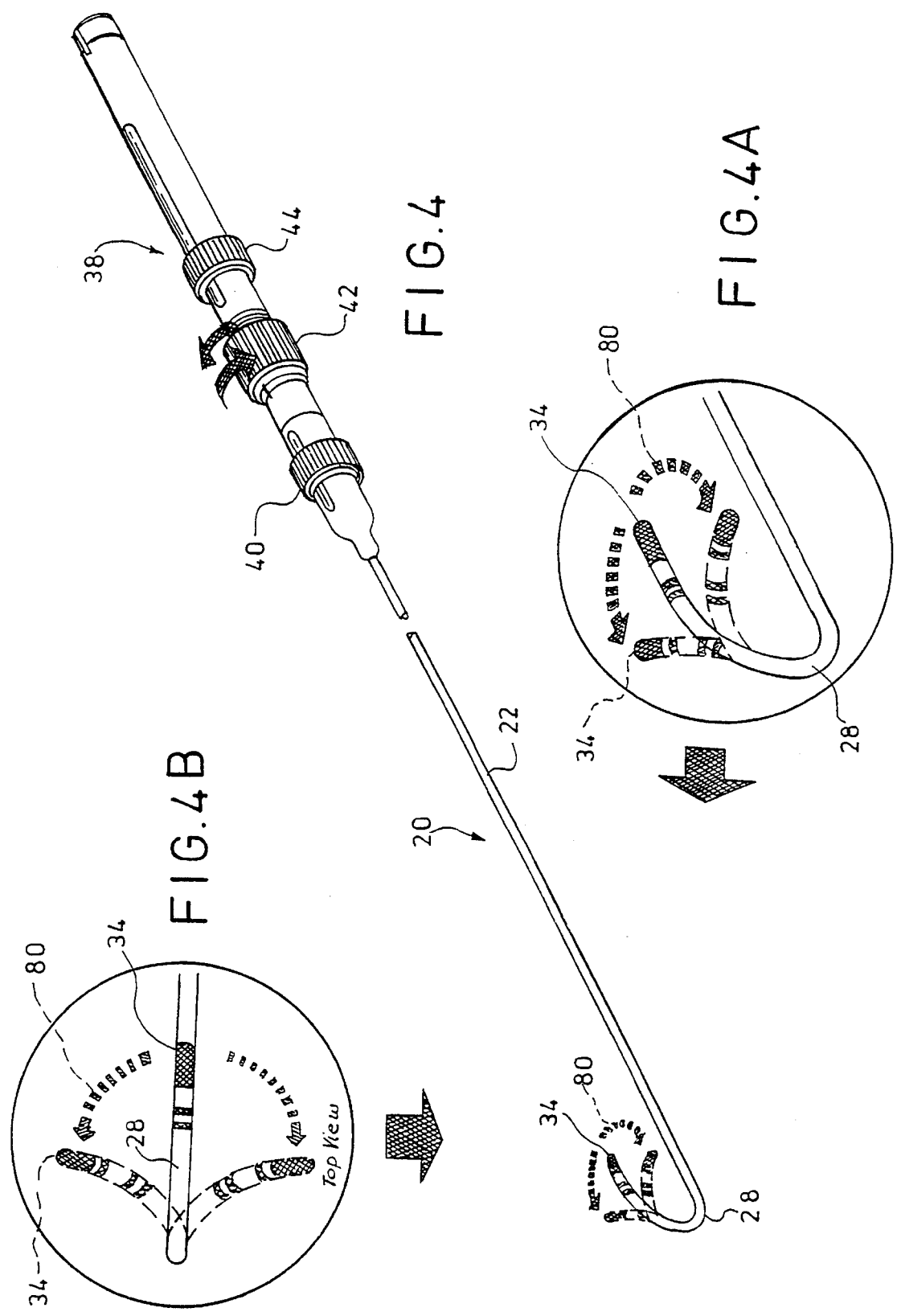

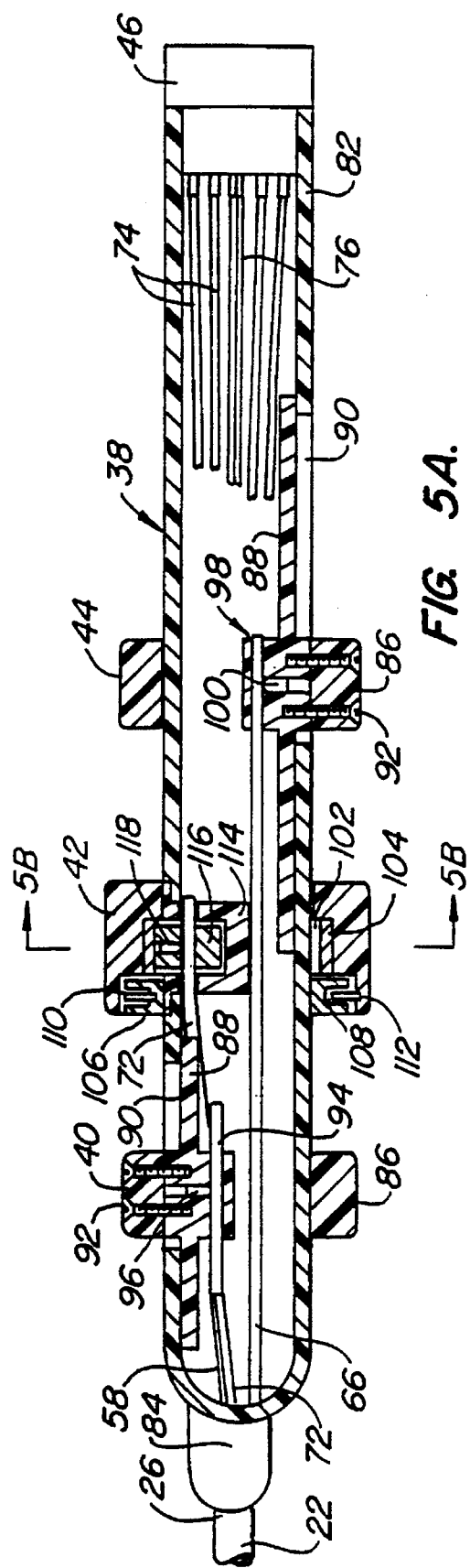
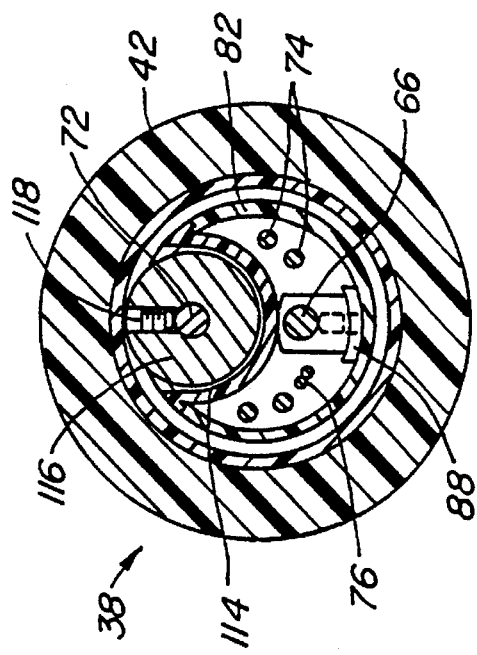
FIG. 5A.
FIG. 5B.

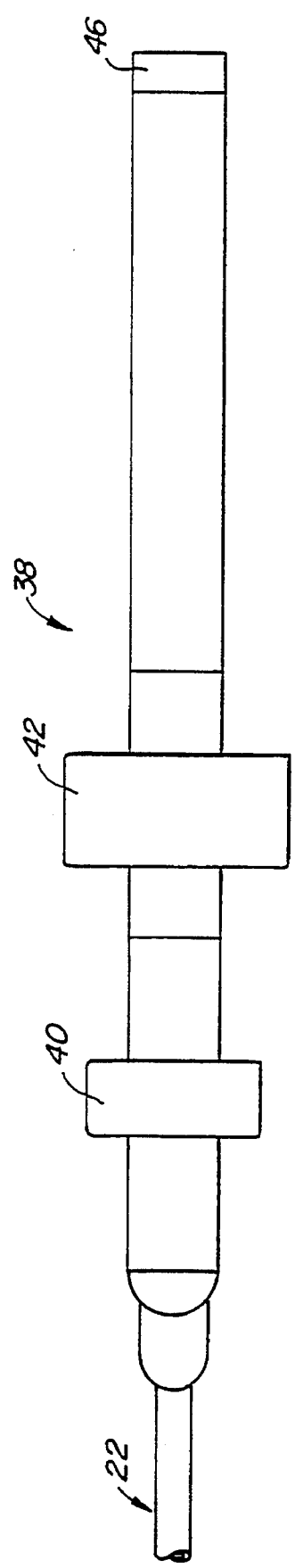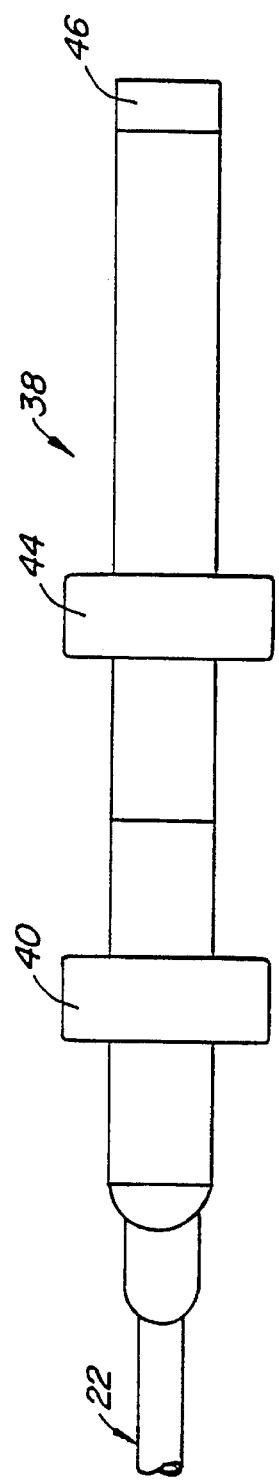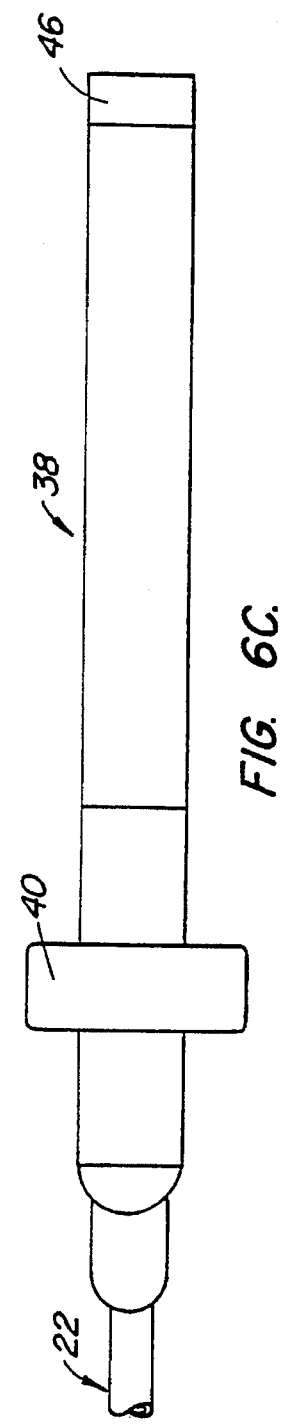

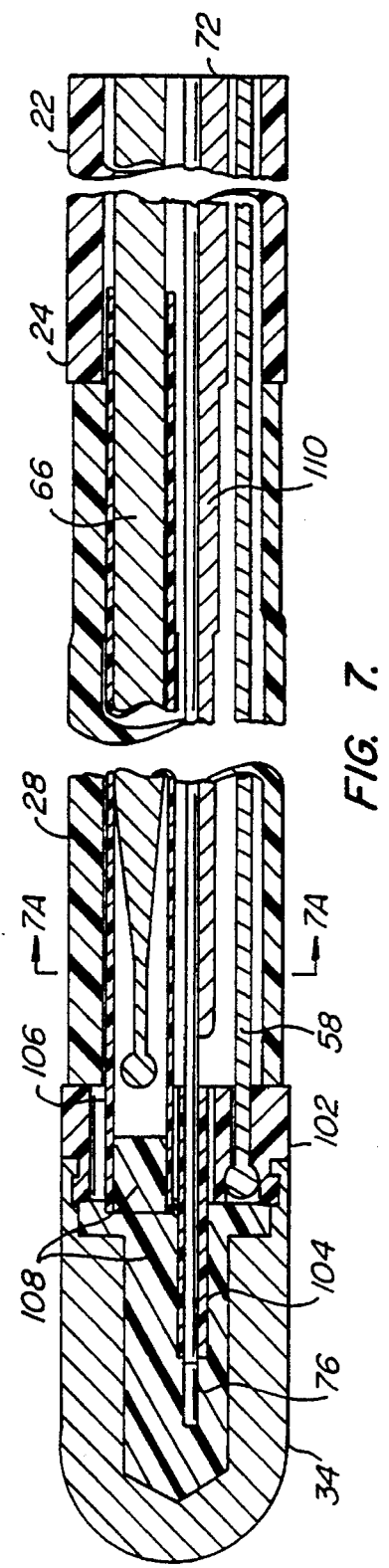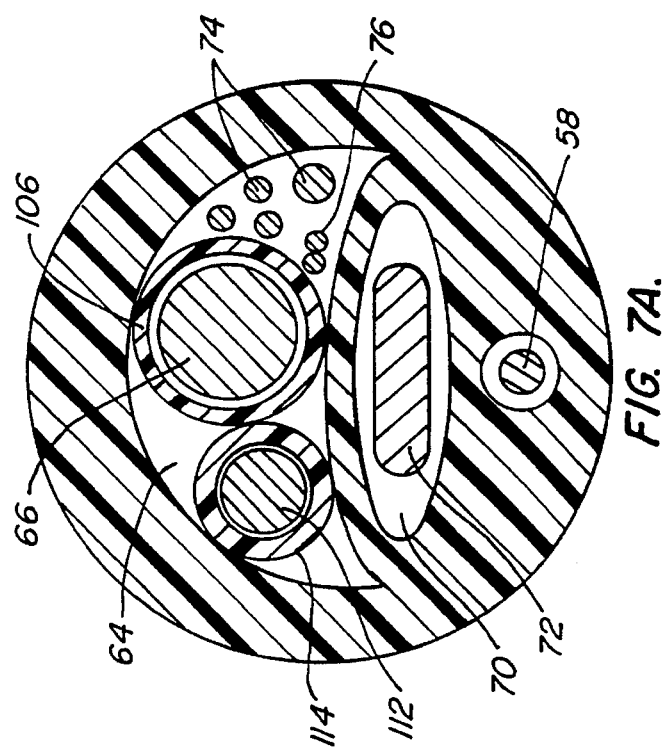
FIG. 7.
FIG. 7A.

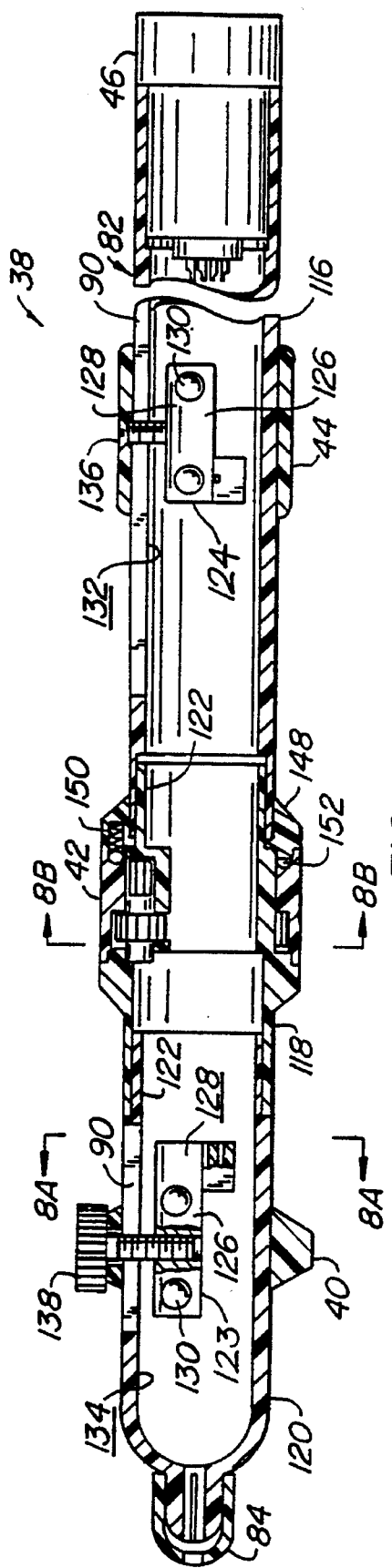
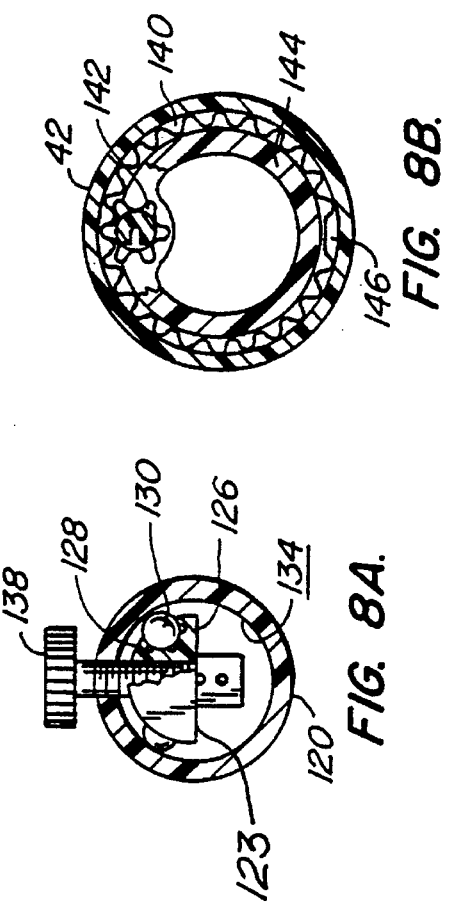
FIG. 8.
FIG. 8A.
FIG. 8B.

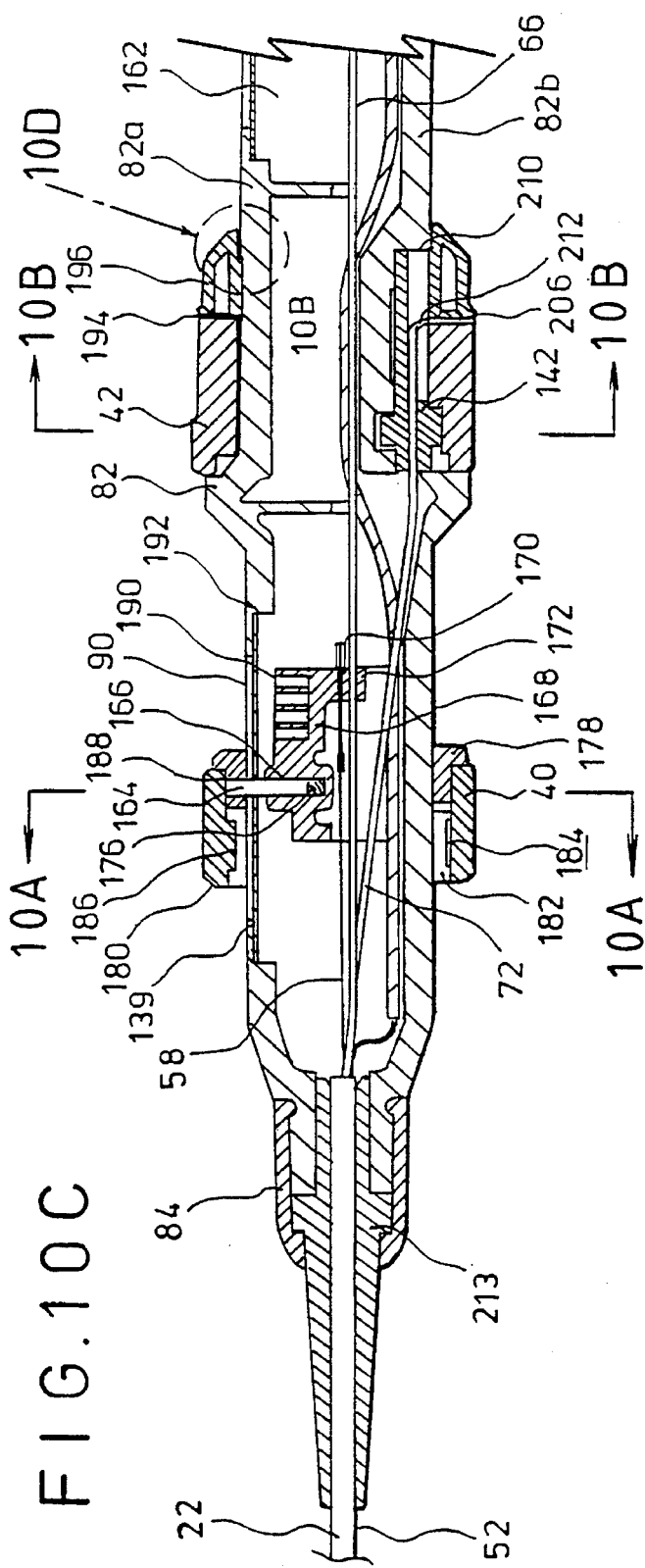
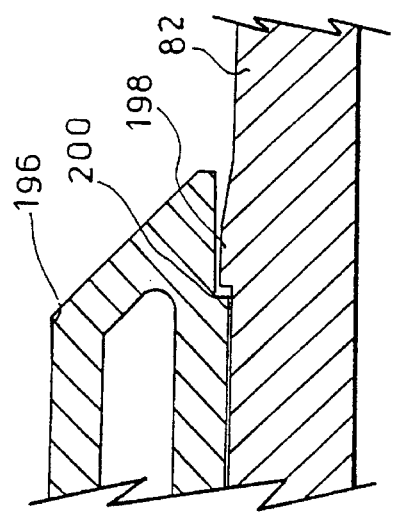
FIG.10C
FIG.10D

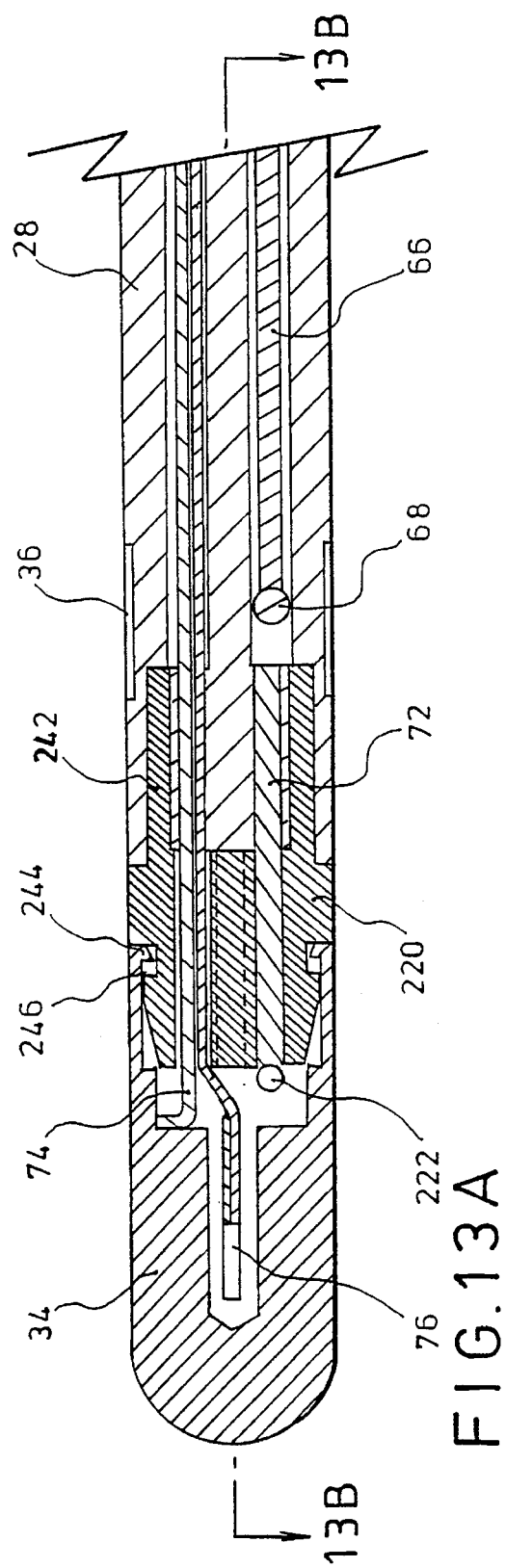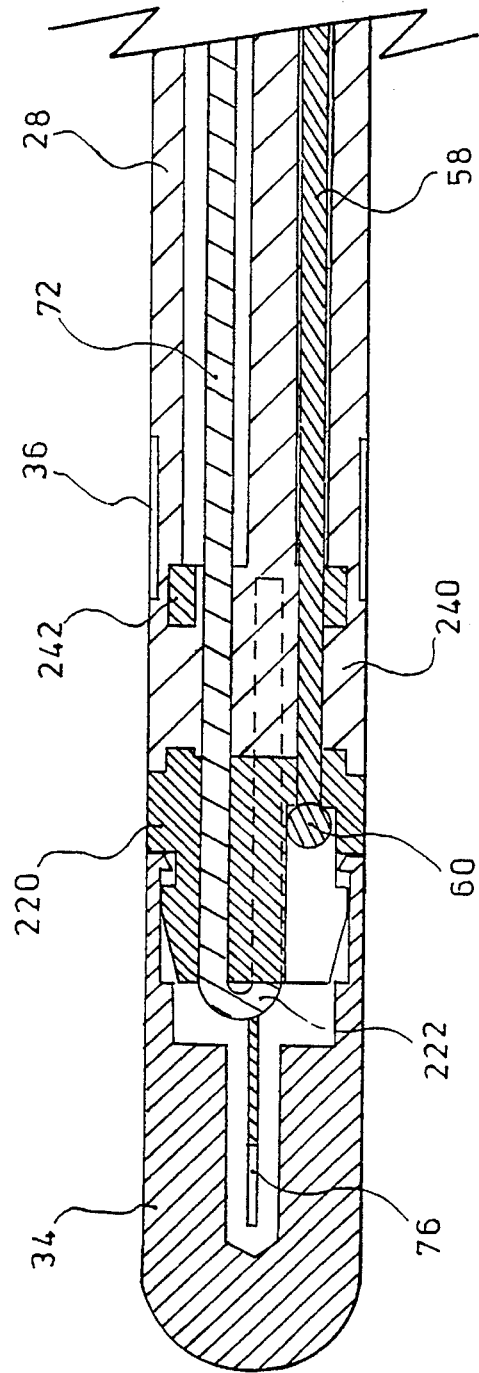
FIG. 13A
FIG. 13B

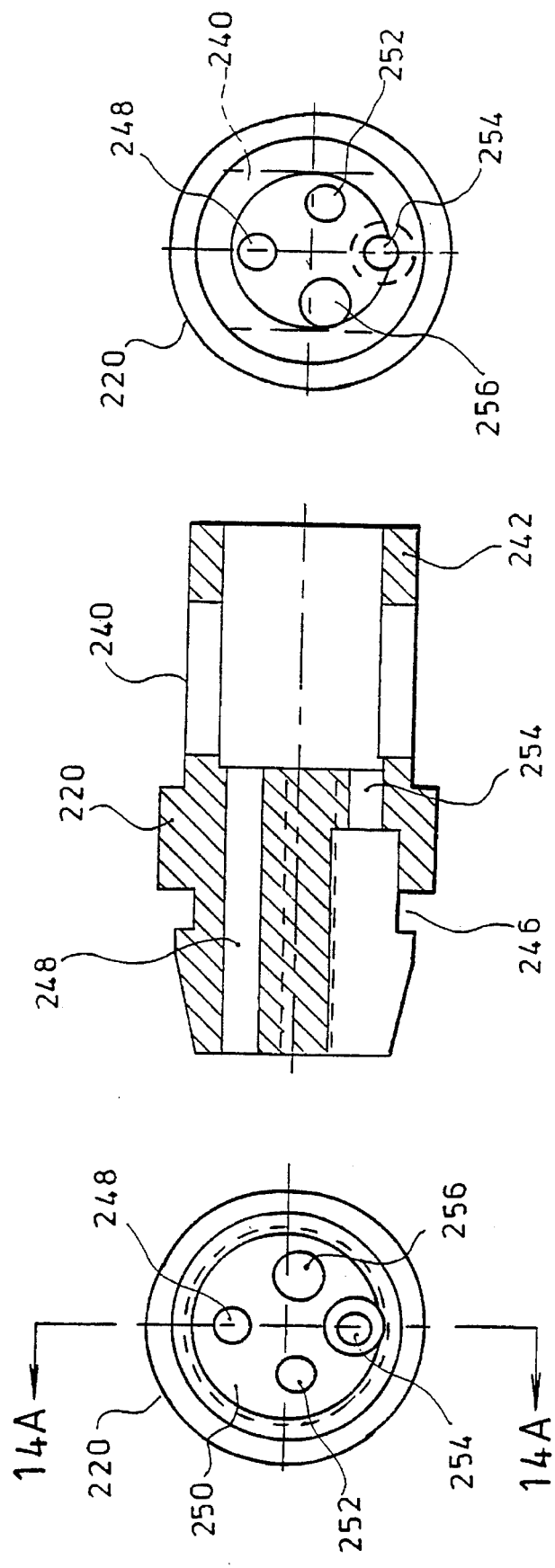

STEERABLE ELECTROPHYSIOLOGY CATHETER

This is a continuation-in-part of U.S. patent application Ser. No. 08/095,447 filed Jul. 20, 1993, now abandoned for Multicurve Deflectable Catheter, the disclosure of which is incorporated by reference.

BACKGROUND OF THE INVENTION

The present invention relates generally to steerable catheters, and more specifically to steerable electrophysiology catheters for use in mapping and ablation of the heart.

The heart includes a number of pathways which are responsible for the propagation of signals necessary for normal, electrical and mechanical function. The present invention is concerned with treatment of tachycardia, abnormally rapid rhythms of the heart caused by the presence of an arrhythmogenic site or accessory pathway which bypasses or short circuits the nodal pathways in the heart. Tachycardias may be defined as ventricular tachycardias (VTs) and supraventricular tachycardias (SVTs). VTs originate in the left or right ventricle and are typically caused by arrhythmogenic sites associated with a prior myocardial infarction. SVTs originate in the atria and are typically caused by an accessory pathway.

Treatment of both ventricular and supraventricular tachycardias may be accomplished by a variety of approaches, including drugs, surgery, implantable pacemakers/ defibrillators, and catheter ablation. While drugs may be the treatment of choice for many patients, drugs typically only mask the symptoms and do not cure the underlying cause. Implantable devices, on the other hand, usually can correct an arrhythmia only after it occurs. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radiofrequency electrical energy, laser energy, and the like.

Of particular interest to the present invention, are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the accessory pathway. By successfully destroying that tissue, the abnormal signaling patterns responsible for the tachycardia cannot be sustained. Methods and systems for performing RF ablation by controlling temperature at the ablation site are described in co-pending application Ser. No. 07/866,683 entitled "Method and System for Radiofrequency Ablation of Cardiac Tissue," filed Apr. 10, 1992 the complete disclosure of which is hereby incorporated by reference.

Catheters designed for mapping and ablation frequently include a number of individual electrode bands mounted to the distal tip of the catheter so as to facilitate mapping of a wider area in less time, or to improve access to target sites for ablation. Such catheters are described in U.S. Pat. No. 5,318,525 issued Jun. 7, 1994 for Steerable Electrode Catheter, the complete disclosure of which is incorporated herein by reference. As described in that patent, it is frequently desirable to deflect the distal tip of the catheter into a non-linear configuration such as a semicircle, which facilitates access to substantially all of the heart walls to be mapped or ablated. Such deflection may be accomplished through the use of pull wires secured to the distal tip which can be tensioned from the proximal end of the catheter to deflect the tip in the desired configuration. In addition, mapping and ablation catheters may facilitate rotational positioning of the distal tip, either by rotating the entire catheter from the proximal end, or, in the catheter described in U.S. Pat. No 5,318,525, by exerting torque on a core wire secured to the distal tip without rotating the catheter body itself.

Catheters utilized in radiofrequency ablation are inserted into a major vein or artery, usually in the neck or groin area, and guided into the chambers of the heart by appropriate manipulation through the vein or artery. Such catheters must facilitate manipulation of the distal tip so that the distal electrode can be positioned against the tissue region to be ablated. The catheter must have a great deal of flexibility to follow the pathway of the major blood vessels into the heart, and the catheter must permit user manipulation of the tip even when the catheter is in a curved and twisted configuration. Because of the high degree of precision required for proper positioning of the tip electrode, the catheter must allow manipulation with a high degree of sensitivity and controllability. In addition, the distal portion of the catheter must be sufficiently resilient in order to be positioned against the wall of the heart and maintained in a position during ablation without being displaced by the movement of the beating heart. Along with steerability, flexibility, and resiliency, the catheter must have a sufficient degree of torsional stiffness to permit user manipulation from the proximal end.

While mapping and ablation catheters having the aforementioned deflectability and steerability have had promising results, such catheters suffer from certain disadvantages. One such disadvantage is the inability to select a desired curvature of deflection in the distal tip. In known catheters, the curvature in the distal tip is determined by the degree of bending stiffness of the distal tip and the degree of tension exerted on the pull wires coupled to it. In any one catheter, the curvature achieved in the distal tip will be the same for any given amount of tension exerted on the pull wires. Thus, if the user desires a particular shape in the distal tip, for example, a semicircle, a particular amount of tension must be exerted on the pull wires, and the semicircular curvature assumed by the distal tip will always have the same radius. Because of the variation in the size of the heart among various patients, as well as the various locations in which a mapping or ablation site may be disposed, it may be discovered during a procedure that the curvature of a given catheter is unsuitable, requiring the catheter to be removed from the patient and replaced with another catheter of suitable configuration.

For these and other reasons, a steerable electrophysiology catheter for use in mapping and ablation is desired which facilitates selective adjustment of the curvature of the distal tip, and which has improved positionability, particularly in rotational positioning. More specifically, the electrophysiology catheter should permit adjustment of the curvature of the deflectable tip without removing the catheter from the patient. The catheter should further have the steerability, flexibility, resilience and torsional stiffness required for transluminal positioning in the heart and accurate guidance of the electrodes to a target site. In addition, when the distal tip is in a deflected configuration, the catheter should be rotationally positionable without rotating its proximal end. This would permit fine control of tip positions without gross rotational movements of the shaft. Since the entire catheter shaft would not need to rotate to cause the laterally deflected tip to move about the longitudinal axis, much less friction would need to be overcome so to permit smooth, fine, precise movements of the tip.

SUMMARY OF THE INVENTION

The invention provides a steerable electrophysiology catheter and a method of electrophysiological treatment which have significant advantages over previous devices and methods. In particular, the device and method of the invention facilitates selective adjustment of the curvature of deflection in the tip without removing the catheter from the patient. In addition, the device and method allow the deflected tip to be rotated about a longitudinal axis without rotating the entire catheter shaft to enhance the ability for fine positioning of the tip.

In a preferred aspect of the invention, a steerable electrophysiology catheter comprises a shaft with a first bending stiffness, the shaft having a proximal end, a distal end, and an axial lumen therebetween. A deflectable tip with a second bending stiffness less than the first bending stiffness has a proximal end secured to the distal end of the shaft, a distal end, a first radially offset axial lumen and a second axial lumen in communication with the axial lumen of the shaft. At least one electrode is secured to the deflectable tip. An appropriate conductor is provided for delivering current from the proximal end of the shaft to the electrode. At least one manipulator wire extends through the axial lumen of the shaft and the first axial lumen of the deflectable tip, and has a distal end secured near the distal end of the deflectable tip and a proximal end near the proximal end of the shaft. Axial force is applied to the manipulator wire at the proximal end of the shaft to deflect the deflectable tip into a first curvature. A stiffener wire is slidably disposed in the axial lumen of the shaft and the second axial lumen of the deflectable tip. The stiffener wire has a bending stiffness such that, when advanced into a section of the tip, the stiffener wire increases the stiffness of such tip section to a value between the first bending stiffness and the second bending stiffness. The stiffener wire is moved axially relative to the deflectable tip from the proximal end of the shaft such that at least a portion of the deflectable tip assumes a second curvature. By axial translation of the stiffener wire relative to the deflectable tip, a desired degree of curvature may be selected for the deflectable tip according to the size of the heart or location of the target site to be mapped or ablated. The manipulator wire preferably has sufficient columnar strength to permit it to be pushed back through the shaft to re-straighten the shaft.

In an exemplary embodiment, the shaft will include reinforcement embedded in a wall thereof for reinforcing the shaft, giving it the first bending-stiffness. Preferably, the reinforcement comprises a wire mesh embedded in the polymeric wall of the shaft to aid the transmission of torque. The shaft will preferably have a Durometer in the range of 35D to 75D, while the deflectable tip will have a Durometer in the range of 30D to 55D. The stiffener preferably becomes gradually more flexible towards its distal end, but is generally stiff enough to increase the tip stiffness when advanced into the tip. Torsional stiffness can also be enhanced by using a shaft having a high durometer inner tube instead of or in addition to the torque-transmitting reinforcement embedded in the shaft wall.

In a further embodiment, the deflectable tip can be rotated about a longitudinal axis without rotating the proximal end of the shaft. Preferably, this is carried out using a core wire disposed in the axial lumen of the shaft and one of the axial lumens of the deflectable tip, the core wire having a distal end coupled near the distal end of the deflectable tip and a proximal end near the proximal end of the shaft. A torque is exerted on the proximal end of the core wire so as to rotate the deflectable tip. Usually, the deflectable tip will have a third axial lumen, between its proximal and distal ends in communication with the axial lumen of the shaft, in which the core wire is disposed.

In a preferred embodiment the core wire has a symmetrical cross-sectional shape, typically round, and is connected to the distal end of the deflectable tip. This arrangement causes the distal end of the tip, when laterally deflected by pulling on the manipulator wire and then rotated by torquing the core wire, to move in a somewhat irregular, corkscrew-like manner. This out-of-plane deflection has proven advantageous in use since it allows the physician to access areas which would otherwise be quite difficult to reach.

In some situations it may be desired that the distal end of the deflectable tip remain at a substantially constant longitudinal position with the distal end of the deflectable tip remaining substantially within a plane perpendicular to the shaft. To do so, the core wire could have a distal portion with a cross-sectional width and thickness, the width being substantially greater than the thickness. Further, the third axial lumen in the deflectable tip could have a cross-sectional width and height, the width being substantially greater than the height. In this way, the distal portion of the core wire would be trapped within the third axial lumen in the deflectable tip so that the core wire would not rotate relative to the deflectable tip. At the same time, the cross-sectional configuration of the distal portion of the core wire would give the core wire an anisotropic bending characteristic so as to maintain the core wire in alignment with the longitudinal axis, thereby maintaining the longitudinal position of the distal end as the deflectable tip is rotated. The core wire, at its proximal end, would preferably have a round cross-sectional shape for effective torque transmission to the tip with no whip. The proximal end of rectangular distal portion of the core wire could be locked in place in the tip, such as by heat fusing. This would allow the core wire to transmit the torquing force to the tip at this point. This would further help to prevent "flipping" of the core wire as the tip is rotated.

If desired, the distal portion of the core wire could extend through most but not all of the tip, but would not be secured to an anchor plate. This would allow the core wire to move longitudinally within an axial lumen in the tip when the tip is deflected by manipulator wire to improve bending characteristics.

In a preferred embodiment, the catheter will further include a handle coupled to the proximal end of the shaft. In an exemplary embodiment, a first slide is axially slidable on the handle and is secured to the proximal end of the stiffener wire to move the stiffener wire axially. A second slide is axially slidable on the handle and is secured to the proximal end of the manipulator wire to move the manipulator wire axially. Other axial drives, including rack and pinion or a worm gear drive, could be used in lieu of the slides. In addition, a third control for lateral deflection comprises a ring gear which drives a smaller pinion gear. The pinion gear is in turn connected to the core wire. Rotating the ring gear rotates the pinion and core wire, twisting the catheter tip for lateral deflection. Various ring/pinion gear ratios may be employed to produce different tip lateral deflections for a given rotational input. Friction locks or detent elements may be applied to the first and/or second slides so as to hold the stiffener wire and/or manipulator wire in tension with the deflectable tip in a deflected configuration. Similar locks may be applied to the ring/pinion gear mechanism.

In a further preferred embodiment, the handle comprises at least two detachable sections, a first detachable section including the structure for moving the stiffener wire and a second detachable section including the structure for applying force to the manipulator wire. A third detachable section could include structure for rotating the core wire. The detachable sections will preferably comprise universal connectors for connecting the detachable sections to each other. The universal connectors preferably comprise a snap fit adapter, wherein a male snap fitting on one detachable section engages a female snap fitting in another detachable section. In this embodiment, the catheter handle is modular, allowing various detachable sections to be selectively added or removed by the manufacturer depending upon the capabilities desired in the catheter, e.g. deflectability, rotatability, or stiffener control.

In a still further preferred embodiment, the handle comprises a tip deflection slide ring and/or a curvature deflection slide ring which can be locked into place by a simple one handed maneuver by the user. This is preferably accomplished using a collect-like structure having an inner slide ring, with a radially deflectable arm, and an outer ring. The inner slide ring can move axially but not rotate while the outer ring can rotate about the inner slide ring and moves axially with the collect slide ring. The two rings include camming surfaces which cause the radially deflectable arm of the collet slide ring to be biased inwardly against the handle housing according to the relative rotary positions of the inner and outer rings. The user simply adjusts the outer ring to provide the appropriate amount of sliding friction to retain the slide ring in the appropriate axial position. If the surfaces ever wear and fail to provide appropriate friction, the outer ring can merely be tightened against the inner ring to reattain the proper amount of friction.

Another feature of this further preferred embodiment relates to the positioning of the torquer ring. Instead of using a ball detent arrangement to secure the torquer ring in an appropriate rotary position, this embodiment uses a spring washer captured between a stationary retainer ring, which extends from the housing, and the torquer ring. Rotation of the torquer ring creates a frictional drag force on at least one of the faces of the spring washer to allow the torquer ring to remain in place regardless of its rotary orientation. Precise positioning of the torquer ring is not inhibited by the use of spring detents but is infinitely variable.

The core wire in this further preferred embodiment is preferably a floating core wire so that deflection of the tip by the manipulator wire is not hindered by the core wire. This is achieved in this embodiment by having the proximal end of the core wire engage the core wire drive pinion in a manner that the core wire can slide axially through the pinion but is constrained to rotate with the pinion.

A further aspect of the invention is the use of a strain relief of a material which can be heat bonded to the jacket of the shaft thus eliminating the need for an adhesive. This eliminates the problems caused when adhesives break down during reuse. This is preferably accomplished using a strain relief made of the same material as the top coat of the shaft and heat welding the two together to create an excellent bond.

In a preferred aspect of the method of the invention, a catheter is introduced through a vessel so that a distal end of the catheter is positioned in the heart, the catheter having a shaft with a first bending stiffness. An axial force is applied to a manipulator wire coupled to a deflectable tip secured to a distal end of the shaft so as to deflect the deflectable tip in a first curvature, the deflectable tip having a second bending stiffness less than first bending stiffness. A stiffener wire may be axially translated in an axial lumen of the deflectable tip such that the deflectable tip assumes a second curvature. Current is then applied through at least a first electrode on the deflectable tip to a target site on the wall of the heart, for purposes of pacing and/or ablation. For mapping, the one or more electrodes are passive and provide heart electrical signals to an ECG. In one embodiment, the stiffener is translated to a position coextensive with only a proximal portion of the deflectable tip, whereby the proximal portion of the deflectable tip assumes a curvature which is different than a distal portion of the deflectable tip.

The method of the invention may further include rotating the deflectable tip about a longitudinal axis parallel to the shaft without rotating the proximal end of the shaft.

A further understanding of the nature and advantages of the invention may be realized by reference to the remaining portions of the specification and the drawings.

BRIEF DESCRIPTION OF THE DRAWINGS

FIG. 1 is a perspective view of a steerable electrophysiology catheter constructed in accordance with the principles of the present invention;

FIG. 1A is a perspective view of a distal portion of the electrophysiology catheter of FIG. 1;

FIG. 4 is a perspective view of a catheter similar to that of FIG. 1 illustrating the corkscrew-like rotational motion of the deflectable tip imparted by the core wire;

FIGS. 4A and 4B are enlarged perspective and top views of the deflectable tip of FIG. 4;

FIG. 5A is a side cross-sectional view of the handle of the catheter of FIG. 1;

FIG. 5B is a transverse cross-sectional view through line 5B—5B in the handle of FIG. 5A;

FIGS. 6A–6C are schematics of the handle of the catheter of FIG. 1, illustrating various configurations of the detachable handle sections;

FIG. 7 is an enlarged side cross-sectional view of the shaft and tip of an alternative embodiment of the invention;

FIG. 7A is a cross-sectional view taken along line 7A—7A in FIG. 7;

FIG. 8 is an enlarge side cross-sectional view of the handle of an alternative embodiment of the invention without any wires or leads;

FIGS. 8A and 8B are cross-sectional views taken along lines 8A—8B and 8B—8B;

FIG. 10C is an enlarged view of the distal portion of the handle of FIG. 10;

FIG. 10D is an enlarged view taken along line 10D—10D of FIG. 10C showing the structure which locks the retaining ring onto the housing;

FIGS. 13A and 13B are cross sectional views of the tip of the embodiment of FIG. 12 taken at right angles to one another;

FIGS. 14, 14A and 14B are distal end, cross-sectional and proximal end views of the tip insulator connector of FIGS. 13A and 13B.

DESCRIPTION OF SPECIFIC EMBODIMENTS

Figure 2A:
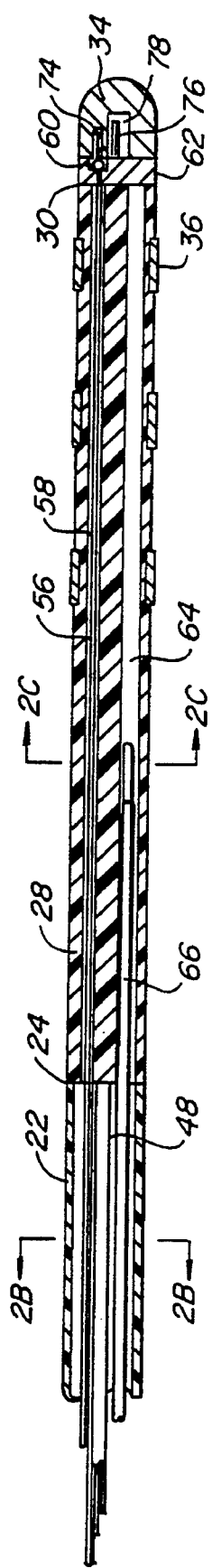
FIG. 2A is a side cross-sectional view of the distal portion of the catheter of FIG. 1.

Electrophysiology catheters constructed in accordance with the principles of the invention will include a shaft, a deflectable tip mounted to the distal end of the shaft and a handle secured to the proximal end of the shaft. The shaft will have an axial lumen extending between its proximal and distal ends. The deflectable tip will have at least two axial lumens, one of the lumens being laterally offset from the central longitudinal axis. At least one manipulator wire will be disposed in the offset axial lumen of the deflectable tip and the axial lumen of the shaft, and will be coupled at its distal end to the distal end of the deflectable tip. Means will be coupled to the handle for applying an axial force to the manipulator wire so as to deflect the distal end of the deflectable tip. The manipulator wire may be configured for either tension or compression to deflect the tip, but usually will be a flexible wire of stainless steel or the like for applying a tensile force to pull on the distal end of the deflectable tip. Such application of tension will cause the deflectable tip to assume a curvature based largely on the degree of bending stiffness of the deflectable tip. Both the shaft and the deflectable tip will have a bending stiffness which is low enough to allow the catheter to be transluminally positioned through a tortuous path into the heart. However, the deflectable tip will have a bending stiffness substantially less than that of the shaft so that the shaft has sufficient column strength to remain substantially undeflected when the manipulator wire is tensioned, and the deflectable tip is sufficiently flexible for deflection into a non-linear configuration of small curvature.

It is desirable to have a smooth transition in stiffness at the junction of the distal end of the shaft and the proximal end of the flexible tip to prevent kinking. This can be accomplished by varying the stiffness of one or both of the flexible tip and the shaft in the regions adjacent their junction, and by varying the stiffness of the stiffener wire and core wire along their lengths.

The catheter will further include a stiffener wire slidably disposed in the axial lumen of the shaft and an axial lumen of the deflectable tip. Means will be provided on the handle for sliding the stiffener wire relative to the deflectable tip, thereby changing the bending stiffness of the deflectable tip according to the position of the stiffener wire. In this way, the deflectable tip may be given a desired curvature by appropriate tensioning of the manipulator wire and/or longitudinal adjustment of the stiffener wire.

In a further aspect of the invention, a steerable electrophysiological catheter will include means for rotating the distal end of the deflectable tip without rotating the proximal end of the shaft, whereby the distal end of the deflectable tip remains in a substantially constant longitudinal position. Preferably, during such rotation, the distal end of the deflectable tip will move in a corkscrew-like manner to permit access to regions which would otherwise be difficult to reach.

Referring now to FIG. 1, electrophysiology catheter 20 includes a shaft 22 having a distal end 24 and a proximal end 26. A deflectable tip 28 is fixed to distal end 24 of shaft 22. Deflectable tip 28 has a distal end 30, and has a plurality of electrodes 32 including a tip electrode 34 and electrode bands 36.

A handle 38 is secured to proximal end 26 of shaft 22. Handle 38 includes a tip deflection slide 40, core wire torquer ring 42 and curvature adjustment slide 44, as well as an electrical connector 46, all described more fully below. As illustrated in FIG. 1A, deflectable tip 28 may be deflected from a straight configuration into a variety of shapes and curvatures, up to at least 270° relative to shaft 22, by adjustment of tip deflection slide 40, curvature adjustment slide 44 and core wire torquer ring 42.

Figure 2C:
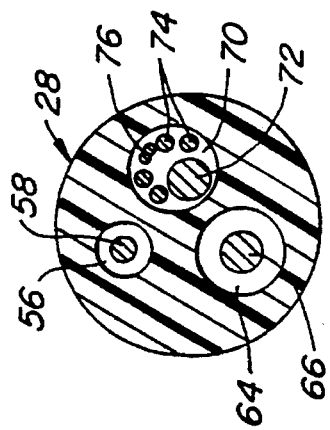
FIGS. 2B and 2C are transverse cross-sectional views taken along lines 2B—2B and 2C—2C, respectively, through the distal portion of the catheter of FIG. 2A.
Figure 2B:
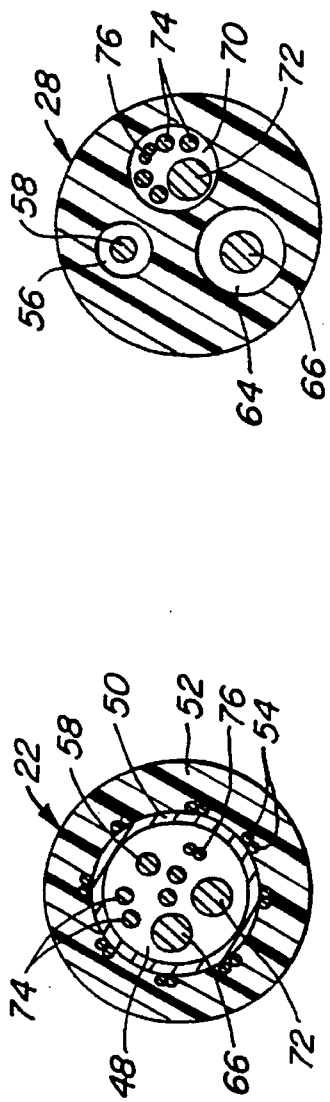

Referring now to FIGS. 2A–2C, shaft 22 has an axial lumen 48 between its proximal and distal ends. The preferred construction of shaft 22 includes a polyimide or ULTEM™ inner tube 50 surrounded by an extruded topcoat 52 of a flexible polymer such as PEBAX. The use of a relatively stiff inner tube 50 within topcoat 52 provides a significant ability to transmit torque along shaft 22. To add additional torsional and bending stiffness to shaft 22, a braided reinforcement 54, usually stainless steel, is embedded in topcoat 52. With this construction, topcoat 52 will have a Durometer reading preferably in the range of 35D to 75D.

Deflectable tip 28 will preferably be a unitary extrusion of a flexible polymer such as PEBAX with a Durometer reading in the range of 30D to 55D. Tip 28 may include internal reinforcement using materials such as polyimide or ULTEM. In a preferred embodiment, the deflectable tip will have three axial lumens extending from its proximal end to its distal end, all in communication with axial lumen 48 in shaft 22. A first axial lumen 56 will be radially offset from the central longitudinal axis of the deflectable tip through which a manipulator wire 58 is disposed. Manipulator wire 58 is coupled at its distal end 60 to an anchor plate 62 at the distal end 30 of deflectable tip 28. Preferably, manipulator wire has a diameter of about 0.15 mm and distal end 60 of the manipulator wire comprises a ball or similar structure for retaining the distal end against anchor plate 62. In a preferred embodiment, axial lumen 56 will be radially offset from the central axis of deflectable tip 28 by an amount equal to approximately 40% to 95% of the radius of the deflectable tip. In an exemplary embodiment, deflectable tip 28 and shaft 22 have a diameter in the range of 5 French (1.65 mm/0.065") to 7 French (2.34 mm/0.092"), with axial lumen 56 being offset in the range of 0.66 mm (0.026") to 2.21 mm (0.087") from the central axis.

In one embodiment, core wire 72 comprises a stainless steel wire with a diameter which ranges from about 0.30–0.64 mm (0.012–0.025"), and preferably about 0.46 mm (0.018"), at its proximal end to about 0.008–0.38 mm (0.007–0.015"), and preferably about 0.20 mm (0.008"), at its distal end for a deflectable tip 28 with diameter of 2.34 mm (0.092").

Deflectable tip 28 includes a second axial lumen 64 in which a stiffener wire 66 is slidably disposed. In a preferred embodiment, stiffener wire 66, when advanced into tip 28, will give tip 28 and wire 66 a combined bending stiffness greater than that of deflectable tip 28 alone, but less than the bending stiffness of shaft 22.

In a preferred embodiment, stiffener wire 66 is TEFLON®-coated stainless steel and has a diameter over most of its length of about 0.30–0.51 mm (0.012–0.020"), and preferably about 0.46 mm (0.018"), tapers down over a length of about 25 mm (1.0") to a diameter of about 0.08–0.25 mm (0.003–0.010"), and preferably about 0.13 mm (0.005"), for the last 13 mm (0.5") of length. The tip of wire 66 also preferably has a ball, of a 0.38 mm (0.015") maximum diameter, welded thereto; the use of the ball helps to prevent accidental puncture of the lumen.

Figure 3B:
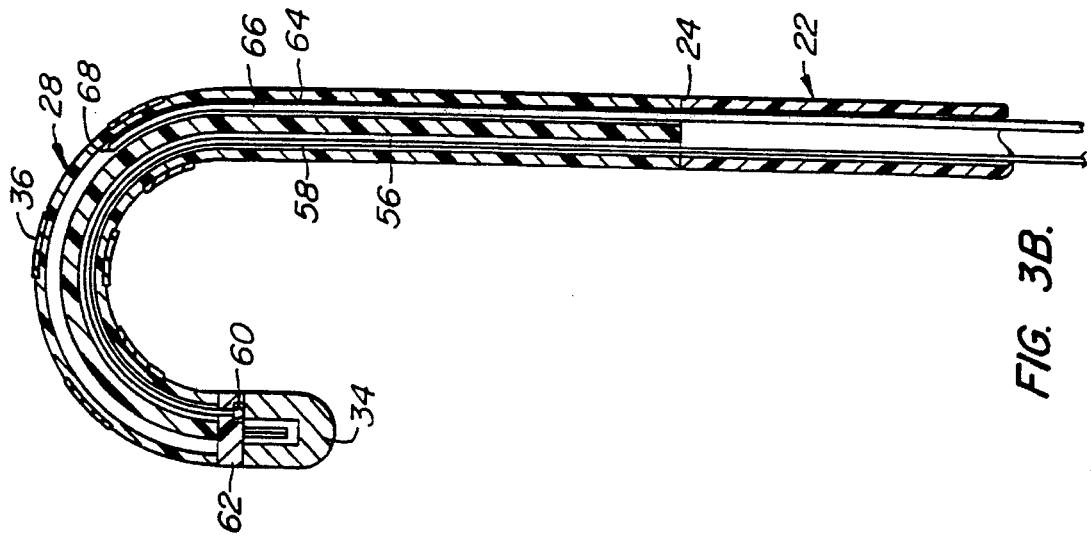
FIGS. 3A and 3B are side cross-sectional views of a distal portion of the catheter of FIG. 1 illustrating two possible tip configurations.
Figure 3A:
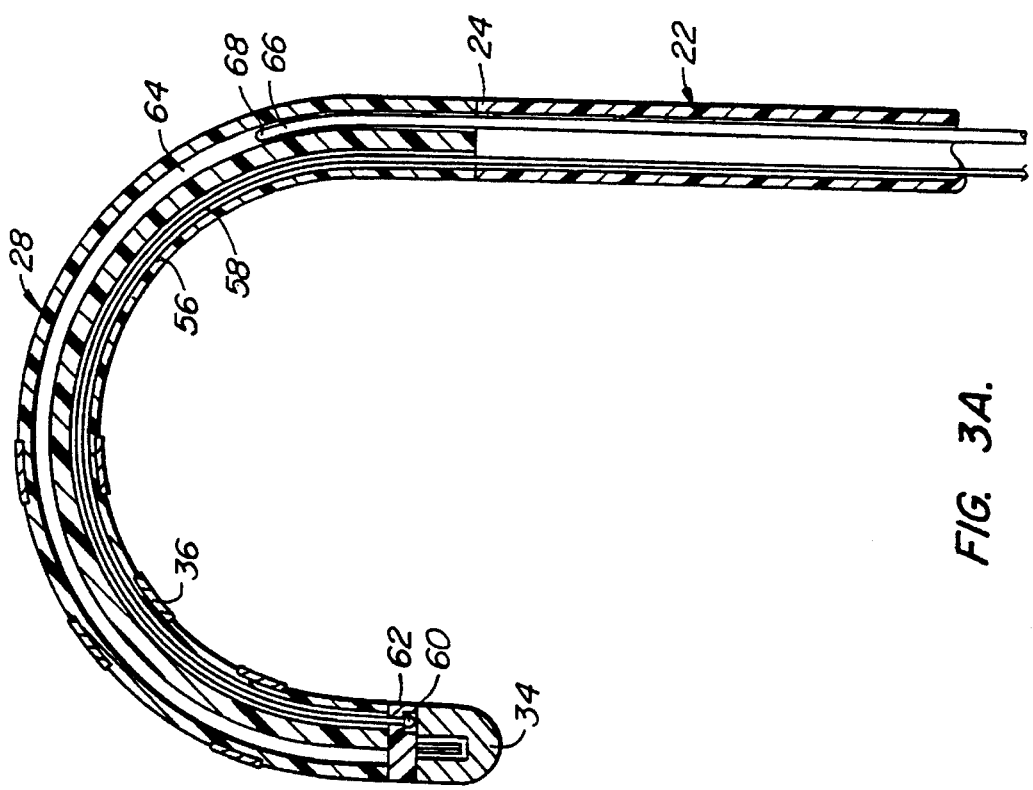

As illustrated in FIGS. 3A and 3B, the curvature imparted to deflectable tip 28 may be selectively adjusted by axially translating stiffener wire 66 within lumen 64, while exerting tension on manipulator wire 58. In the example of FIG. 3A, stiffener wire 66 has been positioned such that its distal end 68 extends into a proximal portion of lumen 64 in deflectable tip 28. The proximal portion of the deflectable tip in which the stiffener wire is disposed therefore has a bending stiffness which is greater than the remaining distal portion of the deflectable tip. By exerting tension on manipulator wire 58, deflectable tip 28 is deflected into a curvature dependent upon the longitudinal position of stiffener wire 66 and the degree of tension applied to the manipulator wire. In FIG. 3B, stiffener wire 66 has been extended distally so that the distal end 68 is closer to the distal end of the deflectable tip. The proximal portion of axial lumen 64 occupied by the stiffener wire is now larger than in the example of FIG. 3A, giving the distal portion of deflectable tip 28 a smaller radius of curvature for a given degree of tension on manipulator wire 58. In this way, when the catheter of the invention has been positioned in the heart, the configuration of the tip can be selectively adjusted to impart the desired curvature and shape to the deflectable tip as appropriate for the size and location of the area to be mapped and/or ablated.

Referring again to FIGS. 2A–2C, deflectable tip 28 further includes a third axial lumen 70 through which a core wire 72 along with electrode wires 74 and thermocouple wires 76 extend. Each of electrode wires 74 is connected to one of electrodes 34, 36. Thermocouple wires 76, typically copper and constantan, extend into an aperture 78 in tip electrode 34 where they are anchored with high temperature adhesive. (As an alternative to stiffener wire 66, an axially extendable tubular stiffener surrounding core wire 72 could be used.)

Core wire 72 extends distally through axial lumen 70 and, in one embodiment, is fixed at its distal end to anchor plate 62. Catheters utilizing such a core wire construction are disclosed in U.S. Pat. No. 5,318,525, the complete disclosure of which has been incorporated herein by reference.

FIGS. 4–4B illustrate a typical corkscrew-like path 80 for tip electrode 34 at the distal end of tip 28. This motion is achieved by first pulling on manipulator wire 58 by pulling on tip deflection slide 40 to deflect electrode 34 laterally and then rotating or torquing core wire 72 by rotating torquer ring 42. This non-uniform path 80 has been found useful by physicians for permitting access to certain hard-to-reach areas. For example, mapping and ablation around mitral and triscupid valve annulus, especially the free wall areas.

Referring now to FIGS. 5A and 5B, handle 38 will be described in greater detail. Handle 38 includes a housing 82, usually cylindrical in shape, constructed of a rigid material such as ABS, nylon, polycarbonate or polystyrene. Shaft 22 is fixed to housing 82 by means of a mechanical grip or an adhesive and incorporating a strain relief 84. Deflection adjustment slide 40 and curvature adjustment slide 44 have similar construction. Slides 40, 44 include an outer ring 86 disposed about the periphery of housing 82 so as to slide axially thereon. Slots 90 extend axially along housing 82 and are in communication with the interior of the housing. Slide backing plates 88 are disposed in the interior of housing 82 and, in this embodiment, longer than slots 90. Rings 86 are fixed to slide backing plates 88 by means of screws 92, whereby friction between backing plates 88 and the interior of housing 82 may be increased by tightening screws 92. With respect to deflection adjustment slide 40, a hypotube 94 is secured to slide backing plate 88, and manipulation wire 58 extends through hypotube 94. Wire 58 and hypotube 94 are joined such as by crimping, or using an adhesive. A screw 96 in backing plate 88 is tightened to frictionally retain hypotube 94. In the case of curvature adjustment slide 44, stiffener wire 66 extends directly through a bore 98 in slide backing plate 88 and is retained therein by aset screw 100. It may be seen that by sliding deflection adjustment slide 40 and curvature adjustment slide 44 axially along slots 90, the deflection of the deflectable tip 28 may be appropriately adjusted. The deflected shape of the tip may be retained by appropriate tightening of screws 92 so that backing plates 88 frictionally engage the interior of housing 82. Sliders 88 act to cover slots 90 to prevent fluid ingress. If desired, flexible external bellows or low Durometer wipers can be used to cover slots 90 allowing the use of shorter sliders 88. Instead of sliders 88, other types of drivers, such as rack and pinion or worm gear drivers, could be used.

Core wire torquer ring 42 is rotatably coupled to housing 82. Torquer ring 42 defines an annular aperture 102 in which is disposed a friction ring 104 of rubber or other high friction material secured to the torquer ring. A limiter ring 106 is fixed to the periphery of housing 82 and defines an annular channel 108. A pin 110 is fixed in a radial position in annular channel 108 and is configured to engage a pin 112 fixed to torquer ring 42 extending radially inward within annular channel 108. Engagement of pins 110, 112 with each other thereby limits the rotational motion of torquer ring 42.

Housing 82 includes a partially cylindrical portion 114, see FIG. 5B, for supporting an inner roller 116. Core wire 72 is fixed to inner roller 116 by means of a set screw 118. Inner roller 116 preferably has a knurled outer surface to fictionally engage friction ring 104 bonded to torquer ring 42. In this way, rotation of torquer ring 42 rotates inner roller 116, thereby exerting torque on the proximal end of core wire 72. If desired, and with appropriate structural modifications, the functions of slider 40 and ring 42 could be combined into a single control.

Preferably, torquer ring 42 comprises a ring gear having drive teeth for engaging gear teeth (not shown) on the outer surface of inner roller 116, as described in co-pending application Ser. No. 08/085,220, attorney docket no. 14875-3-1, entitled "Shapable Handle for Steerable Electrode Catheter," filed Jun. 29, 1993, the complete disclosure of which is incorporated herein by reference. See also the embodiments of FIGS. 8 and 10 described below.

Electrode wire 74 and thermocouple wire 76 extend from shaft 22 through the interior of housing 82 and are coupled to electrical connector 46. Connector 46 is configured for connection to a radiofrequency ablation generator, such as that described in co-pending application Ser. No. 07/866,683, the disclosure of which has been incorporated herein by reference. Connector 46 can also be connected to an ECG machine for mapping.

Handle 38 preferably has a modular construction facilitating easy interchange of actuator components, depending upon the capabilities desired in the catheter. As illustrated schematically in FIGS. 6A–6C, handle 38 will preferably comprise at least two detachable sections, each section having a universal fitting for attachment to one of the other sections. Each detachable section will include at least one of the actuators for steering and deflecting the distal tip of the catheter, i.e., tip deflection slide 40, torquer ring 42 or curvature adjustment slide 44. In this way, handle 38 may be assembled to include only the components desired by a particular user, thereby minimizing the size, cost and complexity of the device.

Where deflection, rotation and curvature control are all desired in the catheter, detachable segments having the tip deflection slide 40, torquer ring 42, curvature adjustment slide 44 as well as electrical connector 46 will all be interconnected by means of snap fittings, as shown in FIGS. 1 and 5A. Alternative configurations are illustrated in FIG. 6A–6C. In a first alternative configuration, handle 38 is provided only with the detachable sections having tip deflection slide 40, torquer ring 42 and connector 46. In the alternative embodiment of FIG. 6B, torquer ring 42 is left out, with tip deflection slide 40 being coupled with curvature adjustment slide 44, along with connector 46. In a third embodiment, shown in FIG. 6C, only tip deflection slide 40 is provided in conjunction with connector 46.

FIG. 7 is a view, similar to that of FIG. 2A, of an alternative embodiment of the invention with like reference numerals referring to like parts. The embodiment of FIG. 7 differs from the embodiment of FIG. 2A primarily with reference to the following. An anchor plate 102 is used to couple electrode tip 34 to tip 28. A polyimide tubing 104 is used to guide the passage of the distal ends of thermocouple wires 76 into tip electrode 34. Another polyimide tubing 106 is used to surround that portion of stiffener wire 66 within tip 28. The interior of tip electrode and the distal end of polyimide tubing 106 are both filled with an electrically insulating, thermally conductive adhesive 108. A section 110 of core wire 72 is thermally fused within axial lumen 70 formed in tip 28 adjacent distal end 24 of shaft 22. As can be seen best in FIG. 7A, a wire stiffener 112 is housed within a polyimide tubing 114 within second axial lumen 64. Wire stiffener 112 extends from anchor plate 102 proximally to a point where stiffener overlaps core wire 72. Stiffener 112 is used to help prevent kinking of tip 28 since core wire 72, in this embodiment, does not extend completely to tip electrode 34 or adapter 102. If desired, core wire 72 can have a circular cross-sectional shape along its entire length; also, stiffener 112 and tubing 114 can be omitted if kinking is not expected to be a problem.

Figure 9:
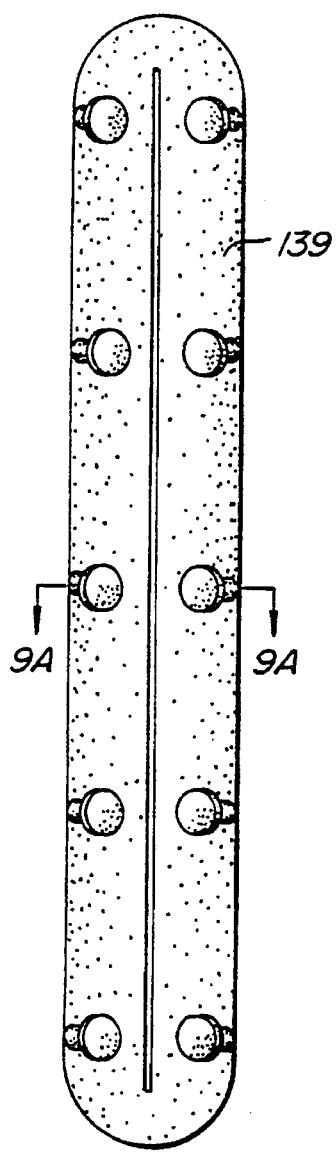
FIGS. 9 and 9A are bottom plan and side cross-sectional views of a wiper-type seal for use with the handle of FIG. 8.
Figure 9A:
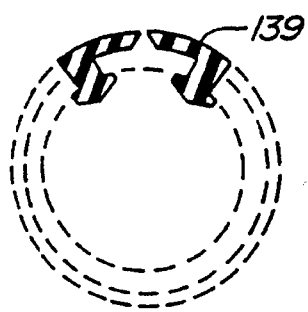

FIG. 8 illustrates an alternative embodiment of handle 38, again with like reference numerals referring to like elements. Housing 82 is shown to include three housing sections 116, 118 and 120. Housing section 118 is mounted to housing sections 116 and 120 using complementary snap-fit joints 122 so that, if desired, housing section 116 can be mounted directly to housing section 120. Instead of backing plates 88, deflection adjustment slider 40 and curvature adjustment slider 44 use front and rear ball sliders 123, 124. Ball sliders 123, 124 each have a semi-cylindrical base 126 having four recesses in its curved outer surface 128 and within which steel balls 130 are mounted. Steel balls ride against the inside surfaces 132, 134 of housing sections 116, 120, respectively. The ball shapes may be formed as integral extensions of base 126. Tightening screws 136, 138 permits the user to adjust the friction between sliders 40, 44 and housing 82. It has been found that ball sliders 122, 124 provide smooth and highly adjustable frictional characteristics. While not shown in this embodiment, fluid shields, such as of the type shown in FIGS. 5A and 5B created by backing plates 88, or by an external bellows type fluid shields, or using external wipers 139 shown in FIGS. 9 and 9A, could be used to cover slots 90 in the embodiment of FIG. 8.

Torquer ring 42 includes an integrally formed internal ring gear 140 which mates with a pinion 142 carried by a torquer housing 144. The proximal end of core wire 72 (not shown in FIG. 8) is secured to pinion 142. Rotation of torquer ring 42 about housing section 118 causes pinion 142 to rotate about its axis as it engages ring gear 140. Ring gear 140 has a missing or filled in tooth 146 to limit the total rotary movement of torquer ring 42, to just under 180° in each direction. Ring gear 140 and pinion 142 have a 4 to 1 ratio so that pinion rotates almost two complete revolutions in either direction. Due to friction and other losses, this causes distal portion 80 of core wire 72 to rotate about 180° in either direction.

Housing section 118 includes a proximal portion 148 which carries three staggered ball detents 150. Ball detents 150 alternately engage a series of indentations 152 formed in the proximally facing edge of torquer ring 42. In the preferred embodiment there are 30 indentations 152 spaced around the periphery of torquer ring 42. Ball detent 150 not only keeps core wire 72 in the desired rotary orientation, but also helps making fine adjustments in the rotary orientation of the core wire 72 and thus of tip 28. Since only one ball detent 150 engages indentations 152 at any one time, a total of 90 different positions are indicated by ball detents 150 engaging indentations 152.

In a preferred aspect of the method of the invention, catheter 20 is transluminally positioned through a blood vessel so that the deflectable tip 28 is within the heart. An axial force is then applied to manipulator wire 58 by sliding tip deflection slide 40 proximally so as to laterally deflect deflectable tip 28 in a first curvature. To further adjust the curvature of the deflectable tip to an optimum configuration, stiffener wire 66 is translated axially relative to the deflectable tip by sliding curvature adjustment slide 44 distally. When the desired degree of curvature has been obtained, deflectable tip 28 may be further positioned rotationally by rotating torquer ring 42, thereby exerting torque on core wire 42 which rotates the deflectable tip about a longitudinal axis. When the electrodes on the deflectable tip have been positioned near a desired target site, radiofrequency current is delivered through connector 46 and electrode wires 74 to electrodes 34, 36, through which current is conducted to the heart tissue to perform ablation. Mapping can be accomplished when catheter 20 is used with an ECG. Advantageously, the catheter may be repositioned and reconfigured in various shapes and curvatures without removing the deflectable tip from the heart, due to the ability to adjust the axial position of stiffener wire 66 in deflectable tip 28. Thus, using the catheter of the invention, virtually any area of the heart may be mapped and/or ablated without removal or interchange of devices.

Figure 10:
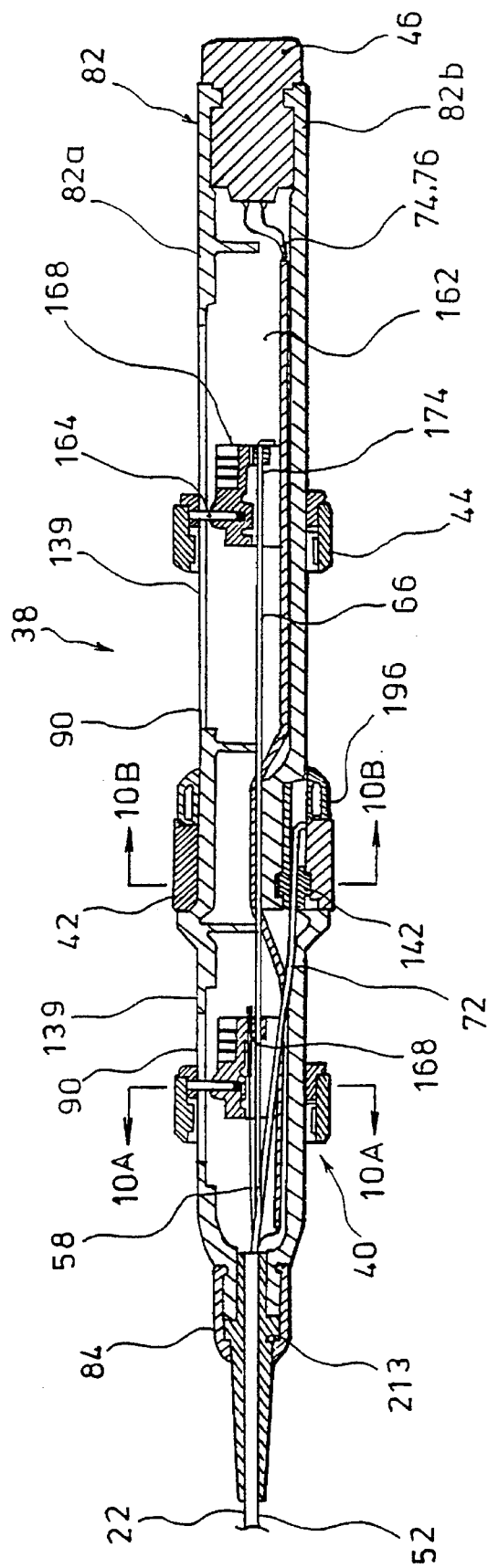
FIG. 10 is cross-sectional view of a still further embodiment of the invention showing a handle similar to the handle of FIG. 8.
Figure 10B:
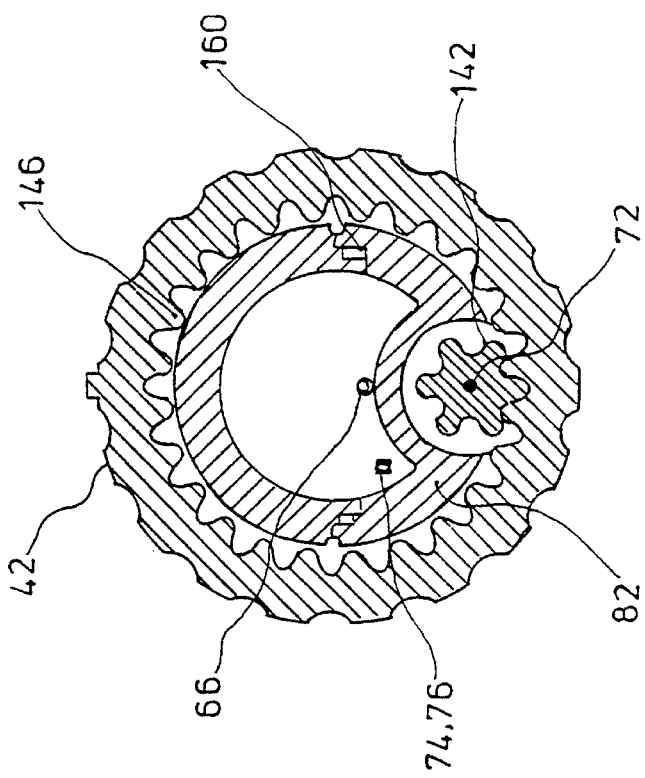
FIGS. 10A and 10B are enlarged cross-sectional views taken along lines 10A—10A and 10B—10B of FIG. 10.
Figure 10A:
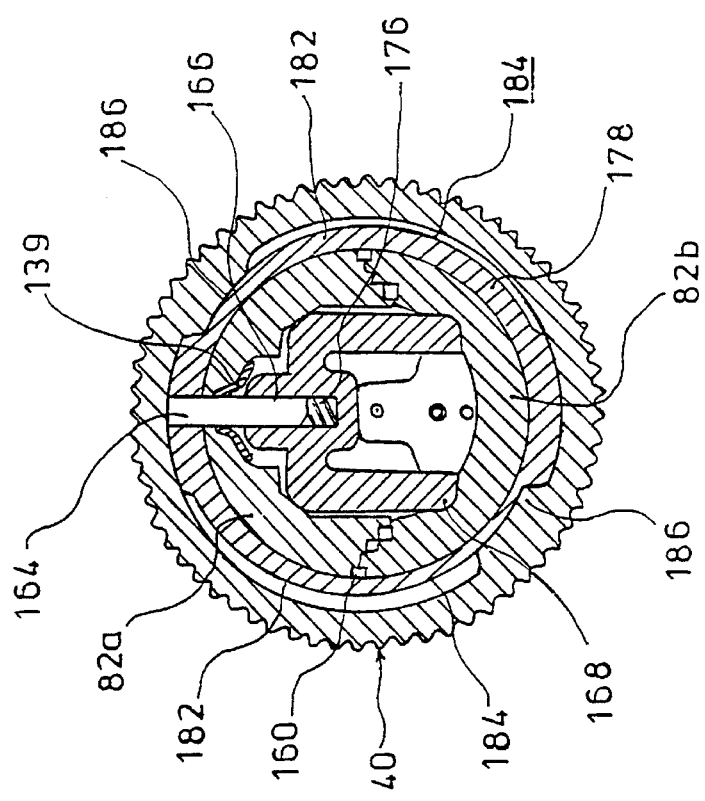

FIGS. 10–10D illustrate a handle 38 of an alternative embodiment of the invention similar to the embodiment disclosed with reference to FIGS. 8–8B. Similar components are referred to with like reference numerals and thus will not be discussed in detail except as necessary or appropriate. Handle 38 includes a housing 82 made of upper and lower housing halves 82a, 82b. The parting lines 160 are not shown in FIG. 10 but are shown in FIGS. 10A and 10B. Housing halves 82a, 82b are preferably joined through ultrasonic welding techniques and capture electrical connector 46 therebetween when so joined. Housing half 82a has a pair of narrow slots 90, each of which is normally sealed by elastomeric wiper 139. The peripheral edges of wiper 139 have a pressure sensitive adhesive which is secured to an inner surface of upper housing 82a thus effectively sealing the interior 162 of housing 82 from the elements. Wipers 139 each have a slit through which a dowel pin 164 passes as shown in FIGS. 10 and 10A.

A dowel pin 164 is slidably mounted within a vertically extending bore 166 formed in a slider 168. The proximal end 170 of manipulator wire 58 is secured to slider 168 while stiffener wire 66 passes a through hole 172 formed in slider 168. The proximal end 174 of stiffener wire 66 is secured to a second slider 168. Dowel pin 164 is biased upwardly by a spring 176 housed at the bottom of bore 166. Pin 164 passes through the slit in wiper 139 and engages tip deflection slider ring 40.

Tip deflection slider ring 40 comprises an inner, slide ring 178 and an outer ring 180. Inner ring 178 includes a pair of radially deflectable arms 182. Arms 182 each have a tapering outer cam surface 184 against which cam riders 186, extending inwardly from outer ring 180, press. By rotating outer ring 180 relative to inner ring 178, cam riders 186 ride along surfaces 184 to bias spring arms 182 of inner ring 178 inwardly against housing 82. The precise amount of friction can thus be adjusted to suit the user and the use.

Dowel pin 164 passes into a hole 188 in inner ring 178 so that axial movement of tip deflection slide ring 40 causes similar axial movement of slider 168 and thus of manipulator wire 58. Slider 168 also has a set of holes 190 within which a limit pin (not shown) could be inserted. The limit pin would serve to limit the maximum movement of slider 168 by contacting a ledge 192 formed at the proximal end of slot 90.

Curvature slide ring 44 is constructed identically to tip deflection slide ring 40 and the slider used with slide ring 44 is identical to the slider 168 used with slide ring 40; accordingly, these components will not be described again.

Figure 11A:
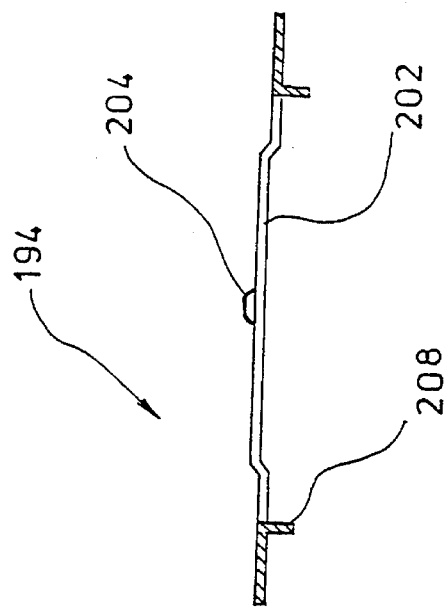
FIGS. 11 and 11A are top plan and cross-sectional views of the spring washer of FIG. 10C.
Figure 11:
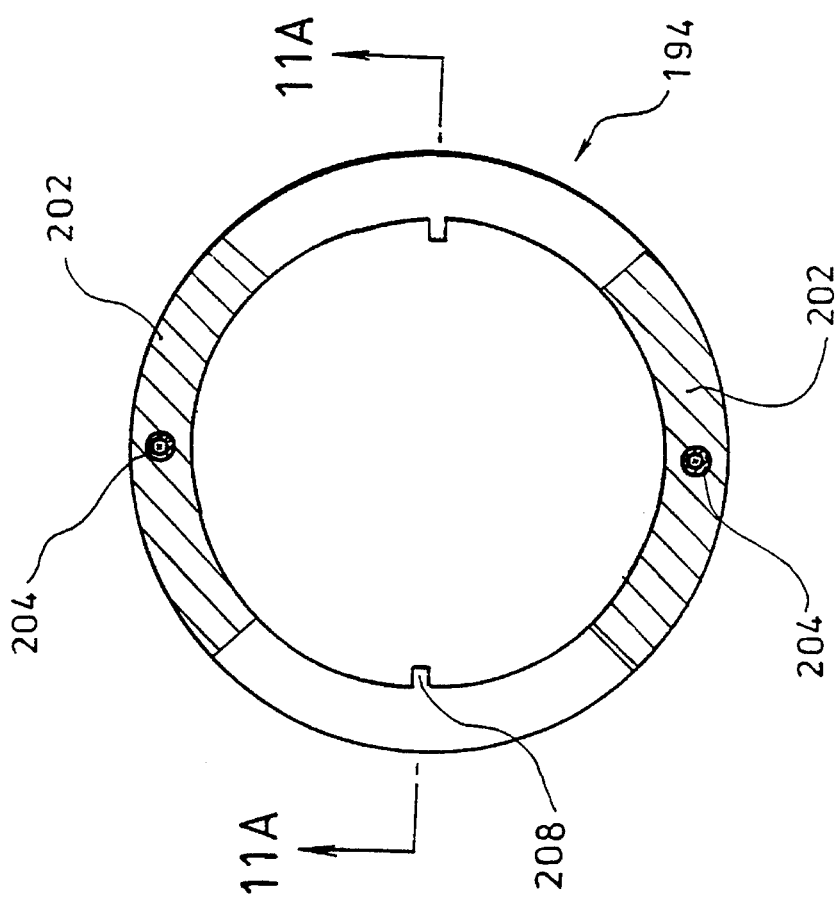

Torquer ring 42 is similar to the torquer ring of FIG. 8. However, instead of using ball detent mechanism to secure torquer ring 42 in the desired rotary position, a spring washer 194, see FIGS. 10C, 11 and 11A, is captured between torquer ring 42 and a retainer ring 196. Retainer 196 can be secured in place, thus compressing spring washer 194 between the abutting surfaces of torquer ring 42 and retainer ring 196, in a variety of ways such as using an adhesive or a set screw. However, the preferred way to keep retainer ring 196 from rotating about housing 82 is by the engagement of a pair inwardly and axially extending ridges (not shown), formed on the inner circumferential surface of ring 196, positioned to engage relatively shallow grooves at parting lines 160. Once in position against spring washer 94, retainer ring 196 is prevented from moving in a proximal direction by the engagement of two small catches 198, extending outwardly from housing 82, with a proximally directed recessed shoulder 200 formed by retainer ring 196. See FIG. 10B.

FIGS. 11 and 11A show spring washer 194 with a pair raised sections 202 each having an upwardly extending bump or dimple 204. Dimples 204 are sized and positioned to mate with two depressions 206 (see FIG. 10C) formed in the surface of torquer ring 42 facing retainer ring 196. Spring washer 194 has a pair of proximally extending tabs 208 which engage the shallow grooves at parting lines 160 to keep spring washer 194 from rotating. This causes dimples 204 to frictionally engage the opposed surface of torquer ring 42 when ring 42 is rotated about housing 82. The friction supplied by engagement of dimples 204 against torquer ring 42 is sufficient to maintain torquer ring 42 in any desired rotary position. However, the engagement of dimples 204 with depressions 206 help to provide a tactile indication of when torquer ring 42 is at the center of its range of travel.

Pinion 142 has a narrow slot 210 which houses the L-shaped proximal end 212 of core wire 72. Accordingly, rotating pinion 142 causes core wire to rotate about its axis, thus creating a torque at tip 28 of catheter 20. However, proximal end 212 is free to slide along slot 210 so manipulation of manipulator wire 58, which causes tip 28 to bend as suggested in FIGS. 1 and 1A, is not hindered by core wire 72. That is, if core wire 72 were to be affixed to pinion 142, movement of manipulator wire 58 in a manner to cause tip 128 to flex would have a tendency to shorten core wire 72; this would be resisted by core wire 72 thus tending to cause deformation of the core wire and possible deformation of shaft 22.

A strain relief 213 is secured within end cap 84 and has shaft 22 passing therethrough. Strain relief 213 is preferably of a material which can be bonded to top coat 52 of shaft 22 without the use of an adhesive. This is preferably accomplished by making strain relief 213 of the same material as top coat 52, such as PEBAX, so they can be heat bonded to one another.

Figure 12B:
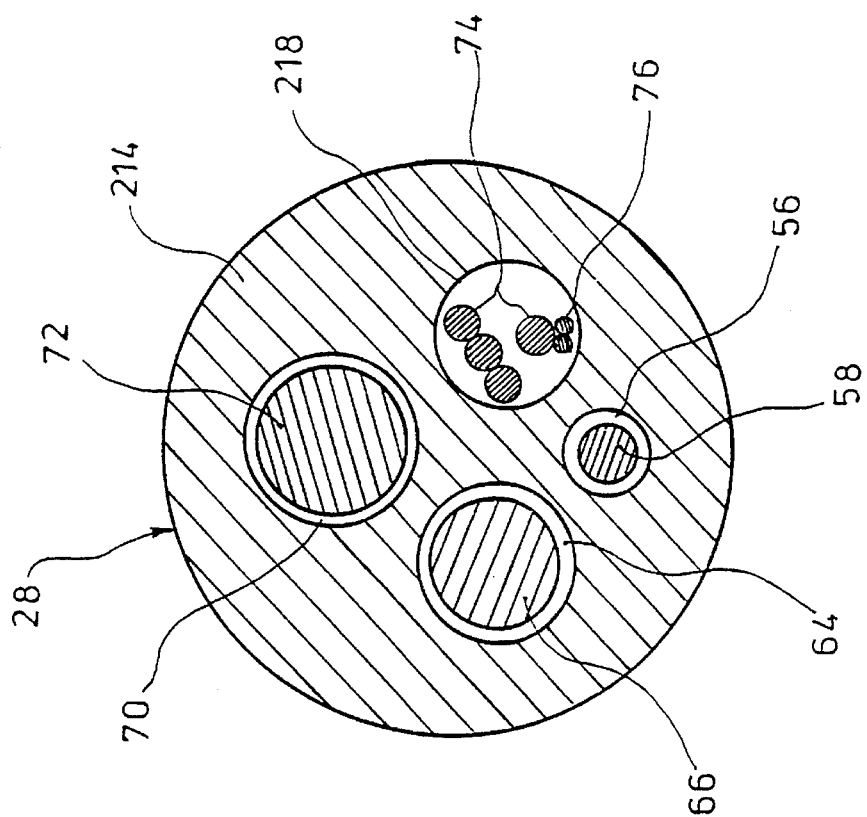
FIGS. 12A and 12B are cross sectional views of sections of an alternative embodiment of the invention similar to the views of FIGS. 2B and 2C, respectively.
Figure 12A:
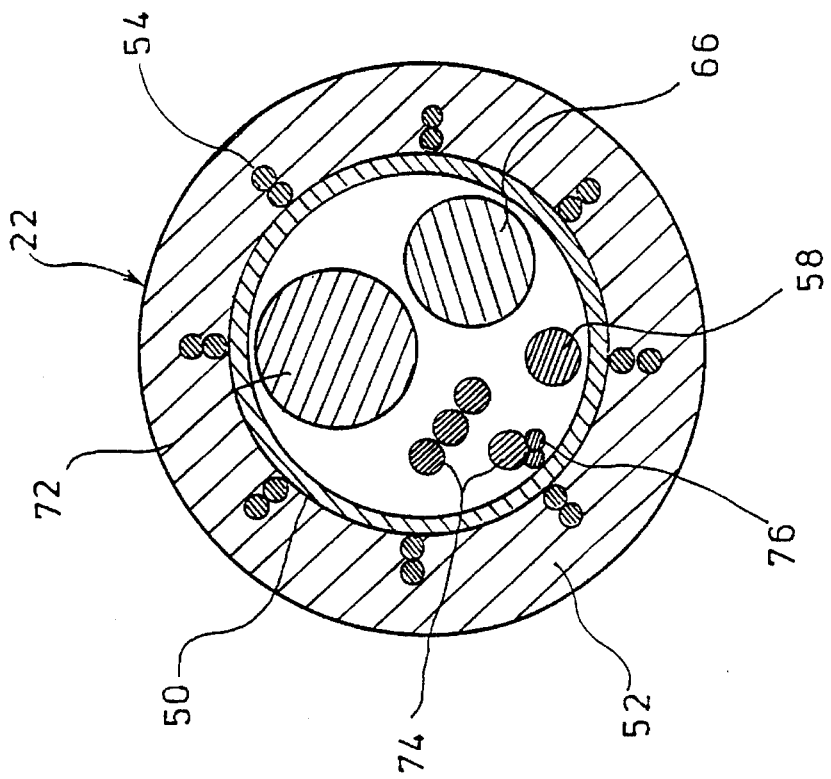

FIGS. 12A and 12B illustrate cross sectional views of the shaft section and the tip section of this embodiment of catheter 22. These cross sectional views have been taken at positions similar to those of 2B and 2C, respectively. While FIG. 12A is similar to FIG. 2B, the structure shown in 12B is somewhat different from that shown in FIG. 2C. Specifically, tip 28 is formed from tip tubing 214, preferably made of PEBAX, having a hardness of about 35 to 45 Shore D, more preferably about 40 D. In addition, tip tubing 214 includes a fourth axial lumen 218 within which electrode wire 74 and thermocouple wires 76 are housed separate from core wire 70. It has been found that separating each of the active wires, that is manipulator wire 58, stiffener wire 66 and core wire 72, in its separate axial lumen in the tip works better by keeping the wires from interfering from one another. Also it is best to separate core wire 70 from manipulator wire 58 so less force is needed to bend the core wire. Separating stiffener wire 66 from electrode and thermocouple wires 74, 76 keep the sliding stiffener wire from possibly damaging the electrode and thermocouple wires.

FIGS. 13A and 13B are cross sectional views of the distal end of catheter 20. Metallic tip electrode 34 is secured to tip 28 by a tip insulator connector 220. See FIGS. 14–14B.

Connector 220 is preferably made of Peek and is secured to tip 28 by a mechanical/thermal bond created by forming radial openings 240 in the central tubular extension 242 of tip insulator connector 220 and heating tip 28 prior to assembly with insulator connector 220; the softened material of tip 28 then flows into bores 240 to provide the desired secure attachment. Tip electrode 34 is secured to connector 220 by a snap fit of an inwardly extending lip 244 at the proximal end of electrode 34 within a recess 246 formed in the connector supplemented by use of an adhesive. Distal end 222 of core wire 72 is passed up through a first bore 248 in connector 200, bent over a ledge 250 formed by connector 220 and passed down through a second bore 252 so that torquing of core wire 72 causes tip 28 to rotate about its longitudinal axis. Connector 220 also includes third and fourth bores 254, 256 which house manipulator wire 58 and electrode and thermocouple wires 74, 76 respectively. The configuration of connector 220 and tip electrode 34 facilitates construction and assembly of the distal end of the catheter.

The use of catheter 22 of FIGS. 10–14 proceeds along similar lines as discussed above. However the axial positions of slide rings 40, 44 are simply and conveniently adjusted through the use of a collet like assembly which allows the user to simply rotate outer ring 180 to achieve the desired degree of holding force. Repositioning rings 40, 44 can be accomplished with or without first loosening outer rings 180 as desired. Slider rings 40, 44 and torquer ring 42 can all be adjusted to any position without regard to predetermined detent settings. Moving manipulator wife 58 axially is accommodated by the axial sliding movement of proximal end 212 of core wire 72 within narrow slot 210 of pinion 142.

Figure 15:
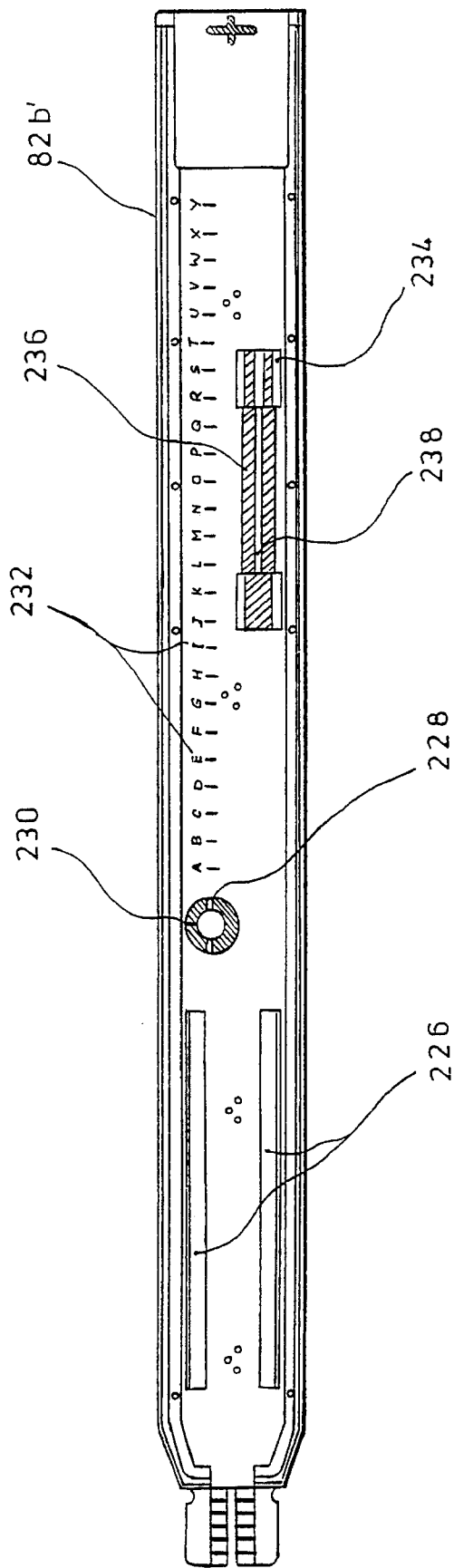
FIG. 15 is a top plan view of the lower housing half of an alternative embodiment of the housing of FIG. 10 in which the tip deflection slide ring is used, the core wire and stiffener wire being secured in chosen positions, typically during manufacture, so not to be changeable by the user.

FIG. 15 illustrates an alternative embodiment of housing half 82b shown in FIG. 10. This housing half 82b' is used when the only adjustment to be made by the user is that for manipulator wire 58. A Slider 168, not shown in FIG. 15, will be supported by tracks 226 formed in housing half 82b' and coupled to a tip deflector slide ring 40 as in embodiment in FIG. 10. Stiffener wire 66 is, however, passed through holes 228 formed in a locking post 230 extending from housing half 82b'. A self tapping screw, not shown, is typically used to secure manipulator wire 15 in position. Housing half 82b' has a series of stiffness indicia 232. Stiffness indicia 232 can be used to adjust the position of stiffener wire 66 within locking post 230 thus adjusting the distance stiffener wire 66 extends within tip 28 to change the radius of curvature as suggested in FIGS. 3A and 3B. Tip stiffness adjustments with this embodiment are not intended to be done by the user but rather during assembly.

Housing half 82b' also has a pair of core wire dowel cradles 234 extending therefrom and sized to support a core wire dowel 236. Core wire dowel 236 serves the same function as pinion 142 of FIG. 10 in that it has a narrow slot 238 within which the L-shaped proximal end 212 of core wire 72 can reside and slide axially but not rotate about its own axis. Accordingly, core wire 72 can be left untorqued or have a predetermined torque applied to it by rotating core wire dowel 236. Core wire dowel 236 is then fixedly secured to dowel cradles 234 such as through a snap or friction fit or through the use of an adhesive. Like with stiffener wire 66, the torque adjustment to core wire 72 is not intended to be a user adjustment in this embodiment of FIG. 15, but is intended to be adjustable during assembly.

While the above is a complete description of the preferred embodiments of the invention, various alternatives, modifications and equivalents may be used. Therefore, the above should not be taken as limiting the scope of the invention, which is defined by the appended claims.

What is claimed is:

1. A steerable electrophysiology catheter comprising:
   a handle;
   a shaft having a proximal end extending from the handle, a distal end, and an axial lumen therebetween;
   a deflectable tip having a proximal end secured to the distal end of the shaft, a distal end and an axial tip lumen in communication with the axial lumen of the shaft;
   at least one electrode secured to the deflectable tip;
   an electrical current path between the handle and the electrode;
   a core wire disposed in the axial lumen of the shaft and the tip lumen, the core wire having a distal end rotatably driveably coupled to the deflectable tip and a proximal end at the handle; and
   the handle comprising a core wire rotator rotatively drivingly coupled to the proximal end of the core wire so to rotate the core wire about its axis thereby rotating the deflectable tip about a longitudinal axis without the need to rotate the proximal end of the shaft.

2. The catheter of claim 1 wherein the proximal end of the tip is secured to the core wire so to transmit torque from the core wire to the tip at the proximal end of the tip.

3. The catheter of claim 1 wherein the core wire is secured to the distal end of the tip so to transfer torque from the core wire to the distal end of the tip.

4. The catheter of claim 3 wherein the core wire has about the same bending stiffness about two perpendicular lines.

5. The catheter of claim 4 wherein the core wire has a circular cross-sectional shape.

6. The catheter of claim 1 wherein the core wire rotater includes a core wire drive element connected to the proximal end of the core wire and a core wire torquer ring rotatably coupled to the core wire drive element and rotatably mounted about the housing for manipulation by a user.

7. The catheter of claim 6 wherein the core wire drive element and the core wire torquer ring include mating gear teeth by which the core wire torquer ring rotates the core wire drive element and the proximal end of the core wire therewith.

8. The catheter of claim 6 wherein the core wire rotater includes:
   a retainer surface adjacent to the core wire torquer ring; and
   a spring washer mounted about the housing and captured between the retainer surface and the core wire torquer ring to create a frictional resistance to the rotation of the core wire torquer ring about the housing and to provide unlimited positional adjustment of said core wire torquer ring.

9. The catheter of claim 1 further comprising a tubular strain relief member acting as an interface between the shaft and the handle, the strain relief member having an inside surface and the shaft having an outside surface, the inside surface of the strain relief and the outside surface of the shaft made of heat weld compatible materials so the strain relief and the tube can be heat weldable to one another without the use of an adhesive.

10. The catheter of claim 1 wherein the core wire rotater includes means for rotatably drivingly engaging the proximal end of the core wire while permitting the proximal end of the core wire to move freely, relative to the handle, in an axial direction.

11. The catheter of claim 1 wherein the at least one electrode includes a tip electrode and a tip insulating connector securing the tip electrode to the shaft.

12. The catheter of claim 11 further comprising means for creating a mechanical/thermal bond between the shaft and the tip insulating connector, said bond creating means including openings formed in the tip insulating connector into which softened shaft material can flow.

13. The catheter of claim 11 wherein the tip insulating connector includes first and second bores within which the distal end of the core wire can be housed to rotatably driveably couple the deflectable tip to the core wire.

14. A steerable electrophysiology catheter comprising:
  a handle;
  a shaft with a first bending stiffness, the shaft having a proximal end extending from the handle, a distal end, and an axial lumen therebetween;
  a deflectable tip with a second bending stiffness less than the first bending stiffness, the deflectable tip having a proximal end secured to the distal end of the shaft, a distal end and an axial tip lumen in communication with the axial lumen of the shaft;
  at least one electrode secured to the deflectable tip;
  an electrical current path between the handle and the electrode;
  a manipulator wire extending through the axial lumen of the shaft and the tip lumen, the manipulator wire having a distal end secured to the deflectable tip and a proximal end at the handle;
  an elongate, flexible stiffener element slidably disposed in the axial lumen of the shaft and the tip lumen, the stiffener element having a third bending stiffness;
  a core wire disposed in the axial lumen of the shaft and the tip lumen, the core wire having a distal end rotatably driveably coupled to the deflectable tip and a proximal end at the handle; and
  the handle comprising:
    a housing;
    a core wire rotater rotatively drivingly coupled to the proximal end of the core wire so to rotate the core wire about its axis thereby rotating the deflectable tip about a longitudinal axis without the need to rotate the proximal end of the shaft;
    a manipulator wire driver axially drivingly coupled to the proximal end of the manipulator wire to apply an axial force to the manipulator wire to deflect the deflectable tip into a first curvature; and
    a stiffener element driver axially drivingly coupled to the proximal end of the stiffener element to axially move the stiffener element relative to the deflectable tip such that at least a portion of the deflectable tip assumes a second curvature.

15. The catheter of claim 14 wherein the core wire is secured to the distal end of the tip so to transmit torque from the core wire to the tip at the distal end of the tip.

16. The catheter of claim 14 wherein the axial tip lumen of the deflectable tip comprises a first, radially offset, axial tip lumen housing the manipulator wire, a second axial tip lumen housing the stiffener element, and a third axial tip lumen housing the core wire.

17. The catheter of claim 16 wherein the stiffener element driver includes:
  a second collet slide ring including:
    an inner ring, coupled to the manipulator wire, having a radially deflectable arm, the inner ring mounted about the housing for axial movement along but not radial movement about the housing; and
    an outer ring rotatably mounted over the inner ring, the inner and outer rings including tapered camming surface means for biasing the arm of the inner ring inwardly against the housing thereby frictionally securing the collet slide ring at a chosen axial position along the housing.

18. The catheter of claim 14 further comprising a tubular strain relief member acting as an interface between the shaft and the handle, the strain relief member having an inside surface and the shaft having an outside surface, the inside surface of the strain relief and the outside surface of the shaft made of heat weld compatible materials so the strain relief and the tube can be heat weldable to one another without the use of an adhesive.

19. A steerable electrophysiology catheter comprising:
  a handle;
  a shaft having a proximal end extending from the handle, a distal end, and an axial lumen therebetween;
  a deflectable tip having a proximal end secured to the distal end of the shaft, a distal end and an axial tip lumen in communication with the axial lumen of the shaft;
  at least one electrode secured to the deflectable tip;
  an electrical current path between the handle and the electrode;
  a manipulator wire extending through the axial lumen of the shaft and the tip lumen, the manipulator wire having a distal end secured to the distal end of the deflectable tip and a proximal end at the handle; and
  the handle comprising a manipulator wire driver axially drivingly coupled to the proximal end of the manipulator wire to apply an axial force to the manipulator wire to deflect the deflectable tip into a first curvature; and
  a tubular strain relief member acting as an interface between the shaft and the handle, the strain relief member having an inside surface and the shaft having an outside surface, the inside surface of the strain relief and the outside surface of the shaft made of heat weld compatible materials so the strain relief and the tube can be heat weldable to one another without the use of an adhesive.

20. A steerable electrophysiology catheter comprising:
  a handle;
  a shaft having a proximal end extending from the handle, a distal end, and an axial lumen therebetween;
  a deflectable tip having a proximal end secured to the distal end of the shaft, a distal end and an axial tip lumen in communication with the axial lumen of the shaft;
  at least one electrode secured to the deflectable tip;
  an electrical current path between the handle and the electrode;
  a manipulator wire extending through the axial lumen of the shaft and the tip lumen, the manipulator wire having a distal end secured to the distal end of the deflectable tip and a proximal end at the handle; and
  a manipulator wire driver mounted to the handle and axially drivingly coupled to the proximal end of the manipulator wire to apply an axial force to the manipulator wire to deflect the deflectable tip into a first curvature; and said manipulator wire driver including a first, axially movable element secured to the manipulator wire, a second element rotatably mounted to the first element and cam means for biasing a chosen one of the first and second elements against the handle so to secure the manipulator wire driver at a chosen axial position according to the rotary orientation of the second element.

21. The catheter of claim 20 wherein the second element is said chosen one of the first and second elements.

22. The catheter of claim 21 wherein said first element is a ring-like element having at least one weakened region to permit a part of the first element to be biased against the handle by the second element.

23. A steerable electrophysiology catheter comprising:
   a handle;
   a shaft with a first bending stiffness, the shaft having a proximal end extending from the handle, a distal end, and an axial lumen therebetween;
   a deflectable tip with a second bending stiffness less than the first bending stiffness, the deflectable tip having a proximal end secured to the distal end of the shaft, a distal end and an axial tip lumen in communication with the axial lumen of the shaft;
   at least one electrode secured to the deflectable tip;
   an electrical current path between the handle and the electrode;
   a manipulator wire extending through the axial lumen of the shaft and the tip lumen, the manipulator wire having a distal end secured to the deflectable tip and a proximal end at the handle;
   a core wire disposed in the axial lumen of the shaft and the tip lumen, the core wire having a distal end rotatably driveably coupled to the deflectable tip and a proximal end at the handle; and
   the handle comprising:
      a housing;
      a core wire rotater rotatively drivingly coupled to the proximal end of the core wire so to rotate the core wire about its axis thereby rotating the deflectable tip about a longitudinal axis without the need to rotate the proximal end of the shaft; and
      a manipulator wire driver axially drivingly coupled to the proximal end of the manipulator wire to apply an axial force to the manipulator wire to deflect the deflectable tip into a first curvature.

24. The catheter of claim 23 wherein the core wire is secured to the distal end of the tip so to transmit torque from the core wire to the tip at the distal end of the tip.

25. The catheter of claim 24 wherein the core wire has about the same bending stiffness about two perpendicular lines whereby torque transmitted to the tip by the core wire causes the tip to move along a path which defines other than a plane perpendicular to axial lumen of the shaft.

26. The catheter of claim 25 wherein the core wire has a circular cross-sectional shape.

27. The catheter of claim 23 wherein the core wire rotater includes means for rotatably drivingly engaging the proximal end of the core wire while permitting the proximal end of the core wire to move freely, relative to the handle, in an axial direction.

28. The catheter of claim 23 wherein the manipulator wire driver is adapted to push and pull the manipulator wire.

29. The catheter of claim 23 wherein the core wire rotater includes a core wire drive element connected to the proximal end of the core wire and a core wire torquer ring rotatably coupled to the core wire drive element and rotatably mounted about the housing for manipulation by a user.

30. The catheter of claim 29 wherein the core wire rotater includes:
   a retainer surface adjacent to the core wire torquer ring; and
   a spring washer mounted about the housing and captured between the retainer ring and the core wire torquer ring to create a frictional resistance to the rotation of the core wire torquer ring about the housing and to provide unlimited positional adjustment of said core wire torquer ring.

31. The catheter of claim 23 wherein the manipulator wire driver includes:
   a collet slide ring including:
      an inner ring, coupled to the manipulator wire, having a radially deflectable arm, the inner ring mounted about the housing for axial movement along but not radial movement about the housing; and
      an outer ring rotatably mounted over the inner ring, the inner and outer rings including tapered camming surface means for biasing the arm of the inner ring inwardly against the housing thereby frictionally securing the collet slide ring at a chosen axial position along the housing.

32. A steerable electrophysiology catheter comprising:
   a handle;
   a shaft with a first bending stiffness, the shaft having a proximal end extending from the handle, a distal end, and an axial lumen therebetween;
   a deflectable tip with a second bending stiffness less than the first bending stiffness, the deflectable tip having a proximal end secured to the distal end of the shaft, a distal end and an axial tip lumen in communication with the axial lumen of the shaft;
   at least one electrode secured to the deflectable tip;
   an electrical current path between the handle and the electrode;
   a manipulator wire extending through the axial lumen of the shaft and the tip lumen, the manipulator wire having a distal end secured to the deflectable tip and a proximal end at the handle;
   an elongate, flexible stiffener element slidably disposed in the axial lumen of the shaft and the tip lumen, the stiffener element having a third bending stiffness; and
   the handle comprising:
      a housing;
      a manipulator wire driver axially drivingly coupled to the proximal end of the manipulator wire to apply an axial force to the manipulator wire to deflect the deflectable tip into a first curvature; and
      means for securing the proximal end of the stiffener element to the handle at a chosen location whereby the curvature of the deflectable tip corresponds the chosen location.

* * * * *